(12) United States Patent
Mathias et al.

(10) Patent No.: US 8,694,312 B2
(45) Date of Patent: *Apr. 8, 2014

(54) DISCRIMINATIVE TRAINING OF DOCUMENT TRANSCRIPTION SYSTEM

(71) Applicant: MModal IP LLC, Franklin, TN (US)

(72) Inventors: Lambert Mathias, Baltimore, MD (US); Girija Yegnanarayanan, Bedford, MA (US); Juergen Fritsch, Pittsburgh, PA (US)

(73) Assignee: MModal IP LLC, Franklin, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/773,928

(22) Filed: Feb. 22, 2013

(65) Prior Publication Data

US 2013/0166297 A1    Jun. 27, 2013

Related U.S. Application Data

(63) Continuation of application No. 11/228,607, filed on Sep. 16, 2005, now Pat. No. 8,412,521, which is a continuation-in-part of application No. 10/922,513, filed on Aug. 20, 2004, now Pat. No. 8,335,688.

(60) Provisional application No. 60/611,171, filed on Sep. 17, 2004.

(51) Int. Cl.
*G10L 15/06* (2013.01)
*G10L 15/26* (2006.01)
*G10L 15/28* (2013.01)

(52) U.S. Cl.
USPC ............ 704/243; 704/235; 704/251; 704/257

(58) Field of Classification Search
USPC .................................. 704/235, 243, 251, 257
See application file for complete search history.

(56) References Cited

U.S. PATENT DOCUMENTS

| | | | |
|---|---|---|---|
| 5,675,707 A * | 10/1997 | Gorin et al. ................... | 704/257 |
| 7,031,908 B1 * | 4/2006 | Huang et al. ...................... | 704/9 |
| 7,236,931 B2 * | 6/2007 | He et al. ......................... | 704/235 |
| 7,324,941 B2 * | 1/2008 | Choi et al. ..................... | 704/255 |
| 8,335,688 B2 * | 12/2012 | Yegnanarayanan et al. .. | 704/235 |
| 8,412,521 B2 * | 4/2013 | Mathias et al. ............... | 704/235 |
| 2002/0123894 A1 * | 9/2002 | Woodward ..................... | 704/260 |
| 2002/0133346 A1 * | 9/2002 | Kemble et al. ................ | 704/257 |

* cited by examiner

*Primary Examiner* — Angela A Armstrong
(74) *Attorney, Agent, or Firm* — Robert Plotkin, P.C.

(57) ABSTRACT

A system is provided for training an acoustic model for use in speech recognition. In particular, such a system may be used to perform training based on a spoken audio stream and a non-literal transcript of the spoken audio stream. Such a system may identify text in the non-literal transcript which represents concepts having multiple spoken forms. The system may attempt to identify the actual spoken form in the audio stream which produced the corresponding text in the non-literal transcript, and thereby produce a revised transcript which more accurately represents the spoken audio stream. The revised, and more accurate, transcript may be used to train the acoustic model using discriminative training techniques, thereby producing a better acoustic model than that which would be produced using conventional techniques, which perform training based directly on the original non-literal transcript.

8 Claims, 15 Drawing Sheets

| | |
|---|---|
| GENERAL HOSPITAL | Date: 10/01/1993 |
| Patient Name: JANE DOE | |
| Chart #: 851D | |

S: Ms. Doe comes in today complaining of a right watery and itchey eye. The patient states that it has been going on for several months now...

PMHx: Significant for hysterectomy, BSO...
Meds: Estratest 1 mg q.d.
Allergies: NKDA.
FamHx: Reviewed.
SocHx: Reviewed.

O: WT: 140  T: 87.6  P: 84  BP: 116/64   GENERAL - The patient is a WDWN white female sitting up in no acute distress...

A: 1. Conjunctivitis, right eye. Suspect allergy, glaucoma cannot be ruled out.

P: 1. The patient is placed on BrandName eyedrops to put two drops in right eye three times a day.
2. The patient also is scheduled an appointment with Dr. Dyer, her optometrist for evaluation of her right eye to rule out possibility of glaucoma.
3. The patient will return if symptoms do not improve. Otherwise, patient will return on next regularly scheduled visit.

SIGNED,
DR. SMITH

DISCRIMINATIVE TRAINING OF DOCUMENT TRANSCRIPTION SYSTEM

CROSS REFERENCE TO RELATED APPLICATIONS

This application is a continuation of U.S. patent application Ser. No. 11/228,607, filed on Sep. 16, 2005, entitled, "Discriminative Training of Document Transcription System", which:
  claims the benefit of U.S. Provisional Pat. App. Ser. No. 60/611,171, filed on Sep. 17, 2004, entitled "Discriminative Training of Acoustic Models Applied to Domains with Unreliable Transcripts"; and which
  is a continuation-in-part of U.S. patent application Ser. No. 10/922,513, filed on Aug. 20, 2004, entitled "Document Transcription System Training".

All of the above-referenced patent applications are hereby incorporated by reference herein.

BACKGROUND

1. Field of the Invention

The present invention relates to document transcription systems, and more particularly, to techniques for training document transcription systems.

2. Related Art

It is desirable in many contexts to record human speech in a written document. In general, the term "transcription" refers to the process of recording speech in a textual document referred to as a "transcript" of the speech. In the legal profession, for example, transcriptionists transcribe testimony given in court proceedings and in depositions to produce a written transcript of the testimony. Similarly, in the medical profession, transcripts are produced of diagnoses, prognoses, prescriptions, and other information dictated by doctors and other medical professionals. Transcripts in these and other fields typically need to be highly accurate (as measured in terms of the degree of correspondence between the original speech and the resulting transcript) because of the reliance placed on the resulting transcripts and the harm that could result from an inaccuracy (such as providing an incorrect prescription drug to a patient). High degrees of reliability may, however, be difficult to obtain consistently for a variety of reasons, such as variations in: (1) features of the speakers whose speech is transcribed (e.g., accent, volume, dialect, speed); (2) external conditions (e.g., background noise); (3) the transcriptionist or transcription system (e.g., imperfect hearing or audio capture capabilities, imperfect understanding of language); or (4) the recording/transmission medium (e.g., paper, analog audio tape, analog telephone network).

At first, transcription was performed solely by human transcriptionists who would listen to speech, either in real-time (i.e., in person by "taking dictation") or by listening to a recording. One benefit of human transcriptionists is that they may have domain-specific knowledge, such as knowledge of medicine and medical terminology, which enables them to interpret ambiguities in speech and thereby to improve transcript accuracy. Human transcriptionists, however, have a variety of disadvantages. For example, human transcriptionists produce transcripts relatively slowly and are subject to decreasing accuracy over time as a result of fatigue.

Various automated speech recognition systems exist for recognizing human speech generally and for transcribing speech in particular. Speech recognition systems which create transcripts are referred to herein as "automated transcription systems" or "automated dictation systems." Off-the-shelf dictation software, for example, may be used by personal computer users to dictate documents in a word processor as an alternative to typing such documents using a keyboard.

Automated transcription systems, and speech recognizers more generally, use both "acoustic models" and "language models" to recognize speech. In general, an acoustic model maps audio signals to phonemes or parts of phonemes. A phoneme is the smallest phonetic unit in a language that is capable of conveying a distinction in meaning, such as the "m" in "mat" and the "b" in "bat." During speech recognition, an acoustic model is used to identify the phonemes represented by portions of the audio signal being recognized. Such a sequence of phonemes may then be combined to recognize the words, sentences, and other syntactic elements spoken by the speaker. Various kinds of acoustic models, such as those which utilize Hidden Markov Models (HMMs), are well-known to those having ordinary skill in the art.

A particular acoustic model represents a particular mapping between speech and text. Although such a mapping could be specified manually by the designer of the transcription system, manual creation of such a mapping would be prohibitively time-consuming and would not likely produce an accurate acoustic model. Instead, acoustic models typically are created using a semi-automated process referred to as "training." The term "training" refers to the process of adapting the parameters of an acoustic model (or of a speech recognition system more generally) for optimal performance in a new domain (e.g., medical or legal) and/or in conjunction with a new speaker.

Referring to FIG. 1A, a dataflow diagram is shown of a prior art system 100 for training a set of acoustic models 112. In the system 100, the acoustic models 112 are trained using a training database 101 consisting of two closely connected data sources: (1) training speech 102 (e.g., in the form of audio recordings of speech) in a particular target domain and/or from a particular speaker; and (2) verbatim transcripts 104 of the speech 102. Because the transcripts 104 are known to be verbatim transcripts of the training speech 102, the combination of the training speech 102 and transcripts 104 implicitly define mappings between phonemes and text, as required by acoustic models. The process of training may be viewed as a process by which these mappings are extracted from the training speech 102 and corresponding transcripts 104 and then represented in a form which may be used subsequently to perform speech recognition on other speech 126 in the same domain. While "speaker dependent" systems can only reliably recognize speech spoken by the speaker of the training speech 102, "speaker independent" systems use training speech spoken by several different speakers, and corresponding transcripts, to train speaker-independent models which may be used to recognize speech from any speaker.

More specifically, a dictionary 108 which maps text to phonetic symbols is used to translate 106 the transcripts 104 into a sequence of dictionary symbols 110 representing the sequence of phonemes in the transcript 104. For example, the sentence "this is a cat" may be translated into the following sequence of dictionary symbols: "dh ih s ih ax k ae t," where each dictionary symbol represents a phoneme in the original sentence.

A base set of acoustic models 112 may be predefined. Each of the acoustic models 112 typically is associated with a set of Gaussian models, each of which has a set of mean values and variances. Before such models 112 have been trained, they may have initial values, such as mean values of zero and variances of some predetermined large number. From the acoustic models 112, a sequence of acoustic models 116 corresponding to the dictionary symbols 110 may be identified 114. More than one acoustic model may correspond to each dictionary symbol.

An association is made between these models 116 and the training speech 102 by aligning 118 the speech 102 onto the sequence of models 116, thereby producing timing data 120 specifying a temporal mapping between the models 116 and frames in the training speech 102. A frame is a short audio segment, typically 5-10 milliseconds in duration. Each of the acoustic models 116 may be aligned with a plurality of frames. In the example provided above, the "ih" models may be assigned to frames from the corresponding sound in speech for the word "this" as well as the same sound in speech for the word "is." Parameters of the models 116 (such as their means and variances) may then be derived from characteristics of the speech 102 in the corresponding frames. Such derivation of acoustic model parameters, and subsequent updating of the acoustic models 112, is referred to as "training" 122 the acoustic models 112. In general, the resulting parameter values indicate probabilities that particular observed sounds represent particular phonemes or parts of phonemes.

The process just described may be repeated for multiple instances of training speech and corresponding verbatim transcripts. Once the acoustic models 112 have been trained in this manner, speech recognition 124 may be performed on other speech 126 by using the trained acoustic models 112 to identify the phonemes that most likely correspond to frames in the speech 126. Text 128 corresponding to the speech 126 may be produced by reversing the mapping going from words to phonemes to models. Because the parameters of the acoustic models 112 were derived from the correspondence between the training text 104 and the training speech 102, speech recognition performed in this way will likely produce poor results if the training text 104 does not accurately represent the training speech 102.

As described above, acoustic models 112 typically are trained based on a training database 101 which includes both recorded utterances 102 and text transcriptions 104 which are known to be verbatim transcripts of the recorded utterances 102. In the dictation domain, for example, the database 101 typically is created by first creating the text 104 and then having speakers speak the text 104 to produce the training speech 102. Text 104 typically is created or collected from existing sources. If a domain-specific acoustic model is desired, such existing sources may be domain-specific sources, such as medical reports if a medical-specific acoustic model is desired. If a generic acoustic model is desired, the existing sources may, for example, be text obtained from a newspaper.

Sections of the training text 104 may then be displayed to a speaker or speakers, who may read the text aloud. A dedicated "speech collection" computer program may record the speech 102 and store it along with the corresponding source text 104, thereby enabling a mapping between source text 104 and spoken utterances 102 to be recorded.

In conversational systems, the training database 101 typically is created by manually transcribing either pre-existing speech or speech created specifically for the purpose of training. For example, chosen subjects may be asked to speak or converse on a given topic. The resulting conversation may be recorded to produce training speech 102, and a human transcriptionist may listen to the spoken recording and produce a verbatim transcript 104 of the speech 102. As a result, an audio file, verbatim transcript of the audio file, and mapping between utterances in the audio file and words in the transcript 104 may be produced.

Regardless of the manner in which the training database 101 is created, the quality of the resulting acoustic models 112 typically is highly reliant on the accuracy of the correspondence between the training speech 102 and the corresponding transcripts 104. In particular, it is typically required that there be an exact or near-exact temporal alignment between the training speech 102 and the corresponding transcripts 104. If such a close temporal alignment does not exist, then the timing data 120 will specify a correlation between text (in the transcripts 104) and audio (in the training speech 102) which do not represent the same speech as each other, and the resulting acoustic models 112 will be poorly trained. Although some training systems are able to identify poorly trained phonemes and to discard the resulting training data (i.e., acoustic model parameters) in response, such an approach reduces the amount of training data, which in turn reduces the accuracy of the resulting acoustic models 112. For these reasons, verbatim transcripts typically are required for conventional acoustic model training to be performed effectively.

It can be difficult to use such training techniques, therefore, in domains in which it is difficult to obtain a large quantity of training speech and corresponding verbatim transcripts. Examples of such domains include the medical and legal domains. In the case of the "prompted speech collection" approach, it may be prohibitively expensive or otherwise impossible to enlist doctors, lawyers, and other professionals who are able to spend the time necessary to recite large amounts of training text 104, and thereby to create the audio recordings 102 necessary to produce the training database 101. Similarly, in the case of the "conversational" approach, the abundance of obscure domain-specific terms in the training speech 102 and the lack of trained medical/legal transcriptionists with knowledge of such terms may make it difficult to produce the large volume of accurate verbatim transcripts 104 that is needed for high-quality training to be performed. In either case, it may be difficult and/or prohibitively expensive to generate the training database 101, given the need for verbatim transcripts 104 of training speech 102 to perform conventional acoustic model training.

In some circumstances, however, large existing bodies of recorded speech and corresponding transcripts may exist. The medical transcription industry, for example, regularly produces a variety of medical reports based on the recorded speech of doctors and other medical professionals. Such reports, however, typically are not suitable for use in the kind of conventional acoustic model training illustrated in FIG. 1A, because such reports typically are not verbatim transcripts of the recorded speech for a variety of reasons.

One reason for a mismatch between the recorded speech and corresponding document is a failure by the transcriptionist to recognize and transcribe the speech accurately. In addition to such errors, however, transcriptionists may intentionally introduce a variety of changes into the written transcription. A transcriptionist may, for example, filter out spontaneous speech effects (e.g., pause fillers, hesitations, and false starts), discard irrelevant remarks and comments, convert data into a standard format, insert headings or other explanatory materials, or change the sequence of the speech to fit the structure of a written report as required by a certain medical institution or physician.

For example, referring to FIG. 12, an example of a structured and formatted medical report 1200 is shown. The report includes a variety of sections 1202-1230 which appear in a predetermined sequence when the report 1200 is displayed. In the particular example shown in FIG. 12, the report includes a header section 1202, a subjective section 1212, an objective section 1224, an assessment section 1226, and a plan section 1228. Sections may include text as well as sub-sections. For example, the header section 1202 includes a hospital name section 1210 (containing the text "General Hospital"), a patient name section 1204 (containing the text "Jane Doe"), a chart number section 1206 (containing the text "851D"), and a report date section 1208 (containing text "10/1/1993").

Similarly, the subjective section includes various subjective information about the patient, included both in text and in a medical history section 1214, a medications section 1216, an allergies section 1218, a family history section 1220, a social history section 1222, and a signature section 1230. The objective section 1224 includes various objective information about the patient, such as her weight and blood pressure. Although not illustrated in FIG. 12, the information in the objective section may include sub-sections for containing the illustrated information. The assessment section 1226 includes a textual assessment of the patient's condition, and the plan subsection 1228 includes a textual description of a plan of treatment. Finally, the signature section includes a textual representation of the doctor's signature.

Note that information may appear in a different form in the report from the form in which such information was spoken by the dictating doctor. For example, the date in the report date section 1208 may have been spoken as "october first nineteen ninety three, "the first of october ninety three," or in some other form. These alternative ways of speaking the same date are referred to herein as "alternative spoken forms" of the date. More generally, each way of speaking a particular concept is referred to herein as a "spoken form" of the concept. The transcriptionist, however, transcribed such speech using the text "10/1/1993" in the report date section 1208, perhaps because written reports in the hospital specified in the hospital section 1210 requires that dates be expressed in reports in such a format.

Similarly, information in the medical report 1200 may not appear in the same sequence in the report 1200 as in the original audio recording, due to the need to conform to a required report format or some other reason. For example, the dictating physician may have dictated the objective section 1224 first, followed by the subjective section 1212, and then by the header 1202. The written report 1200, however, contains the header 1202 first, followed by the subjective section 1212, and then the objective section 1224. Such a report structure may, for example, be required for medical reports in the hospital specified in the hospital section 1210.

The beginning of the report 1200 may have been generated based on a spoken audio stream such as the following: "this is doctor smith on uh the first of october um nineteen ninety three patient ID eighty five one d um next is the patient's family history which i have reviewed . . . . " It should be apparent that a verbatim transcript of this speech would be difficult to understand and would not be particularly useful.

Note, for example, that certain words, such as "next is a," do not appear in the written report 1200. Similarly, pause-filling utterances such as "uh" do not appear in the written report 1200. Furthermore, certain terms, such as dates, have been recorded in the report 1200 using particular canonical forms (e.g., in the report date section 1208). In addition, the written report 1200 organizes the original speech into the predefined sections 1202-1230 by re-ordering the speech. As these examples illustrate, the written report 1200 is not a verbatim transcript of the dictating physician's speech.

Although a report such as the report 1200 may be more desirable than a verbatim transcript for a variety of reasons (e.g., because it organizes information in a way that facilitates understanding), the report is not useful as training text in the traditional acoustic model training process described above with respect to FIG. 1A, precisely because the report 1200 is not the kind of verbatim transcript required for traditional acoustic model training.

In summary, although a large body of existing documents corresponding to speech may be available in certain circumstances, such documents may not be verbatim transcripts of the corresponding speech. If conventional acoustic model training were applied to such speech and corresponding documents, the resulting acoustic models would be sub-optimal, perhaps to such an extent that they would not be suitable for use in speech recognition.

It would be advantageous, however, to be able to use such reports to train acoustic models because of the abundance of existing reports in domains such as medicine and law. Although new, verbatim, transcripts could be generated based on existing recorded spoken audio streams, generating large volumes of such transcripts would be tedious, time-consuming, and costly. Furthermore, it would inefficiently require two transcripts to be generated for each recorded audio stream (one verbatim transcript to be used for acoustic model training, and one non-verbatim transcript to be used for traditional purposes).

Referring to FIG. 1B, a dataflow diagram is shown of a prior art system 150 which attempts to solve the problem just described. The system 150 includes spoken audio 152 and a corresponding non-literal transcript 154 of the audio 152, produced by a transcriptionist 156. As described in more detail below, the non-literal transcript 154 includes information from the audio 152, but is not a literal (verbatim) transcript of the audio 152. An attempt is made, either manually or automatically, to align 158 the audio 152 with the non-literal transcript 154, thereby producing timing data 160 specifying temporal correlations between portions of the audio 152 and text in the non-literal transcript 154.

The audio 152, timing data 160 and non-literal transcript 154 are provided to a confidence filter 164, which measures the degree of "fit" between the frames and corresponding word models. If the fit for a particular frame does not satisfy a confidence threshold, the confidence filter 164 marks the frame as unusable. The confidence filter 164 thereby produces a set of filtered labels 166 which identify the frames that satisfied the confidence threshold. The audio 152, non-literal transcript 154, and filtered labels 166 are provided to a trainer 162, which produces a set of trained acoustic models 168 based on the portions of the spoken audio stream 152 and non-literal transcript 154 identified by the filtered labels 166.

One problem with the approach illustrated in FIG. 1B is that a large amount of training data from the initial acoustic models 164 may be discarded because so much of the non-literal transcript 154 fails to match the corresponding portions of the spoken audio 152. In particular, such an approach may tend to systematically discard training data that do not take the same form as the text in the non-literal transcript 154. For example, if the word "November" in the spoken audio stream 152 is aligned with the text "11" in the non-literal transcript 154, such training data will be discarded even though "November" and "11" represent the same semantic content. If the spoken audio stream 152 consistently contains the word "November" when the non-literal transcript contains the text "11", training data of this kind will consistently be discarded. The approach illustrated in FIG. 1B, therefore, has limited usefulness.

What is needed, therefore, are improved techniques for training speech recognition systems and, in particular, improved techniques for training transcription systems based on non-literal transcripts of speech.

SUMMARY

In one embodiment of the present invention, a system is provided for training an acoustic model for use in speech recognition. In particular, such a system may be used to perform training based on a spoken audio stream and a non-literal transcript of the spoken audio stream. Such a system may identify text in the non-literal transcript which represents concepts having multiple spoken forms. The system may attempt to identify the actual spoken form in the audio stream which produced the corresponding text in the non-literal transcript, and thereby produce a revised transcript which more accurately represents the spoken audio stream. The revised, and more accurate, transcript may be used to train the acoustic model using discriminative training techniques, thereby producing a better acoustic model than that which would be produced using conventional techniques, which perform training based directly on the original non-literal transcript.

For example, in one embodiment a method is provided for use in a system including a first document containing at least some information in common with a spoken audio stream. The method includes steps of: (A) identifying text in the first document representing a concept having a plurality of spoken forms; (B) replacing the identified text with a context-free grammar specifying the plurality of spoken forms of the concept to produce a second document; (C) generating a first language model based on the second document; (D) using the first language model in a speech recognition process to recognize the spoken audio stream and thereby to produce a third document; (E) filtering text from the third document by reference to the second document to produce a filtered document in which text filtered from the third document is marked as unreliable; and (F) using the filtered document and the spoken audio stream to train an acoustic model by performing steps of: (F)(1) applying a first speech recognition process to the spoken audio stream using a set of base acoustic models and a grammar network based on the filtered document to produce a first set of recognition structures; (F)(2) applying a second speech recognition process to the spoken audio stream using the set of base acoustic models and a second language model to produce a second set of recognition structures; and (F)(3) performing discriminative training of the acoustic model using the first set of recognition structures, the second set of recognition structures, the filtered document, and only those portions of the spoken audio stream corresponding to text not marked as unreliable in the filtered document.

The base acoustic models may be trained using the spoken audio stream and the filtered document before performing the first and second speech recognition processes. Such training may, for example, be performed using maximum likelihood optimization training. The discriminative training performed in step (F)(3) may, for example, be maximum mutual information estimation training, wherein the first set of recognition structures comprises a "correct" lattice, and wherein the second set of recognition structures comprises a "general" lattice.

In another embodiment of the present invention, a method is provided which includes steps of: (A) identifying a normalized document of a spoken audio stream, the normalized document including a context-free grammar specifying a plurality of spoken forms of a concept; (B) identifying a language model based on the normalized document; (C) using the language model in a speech recognition process to recognize the spoken audio stream and thereby to produce a second document; (D) filtering text from the second document by reference to the normalized document to produce a filtered document in which text filtered from the second document is marked as unreliable; and (E) using the filtered document and the spoken audio stream to train an acoustic model by performing steps of: (E)(1) applying a first speech recognition process to the spoken audio stream using a set of base acoustic models and a grammar network based on the filtered document to produce a first set of recognition structures; (E)(2) applying a second speech recognition process to the spoken audio stream using the set of base acoustic models and a second language model to produce a second set of recognition structures; and (E)(3) performing discriminative training of the acoustic model using the first set of recognition structures, the second set of recognition structures, the filtered document, and only those portions of the spoken audio stream corresponding to text not marked as unreliable in the filtered document.

The base acoustic models may be trained using the spoken audio stream and the filtered document before performing the first and second speech recognition processes. Such training may, for example, be performed using maximum likelihood optimization training. The discriminative training performed in step (E)(3) may, for example, be maximum mutual information estimation training, wherein the first set of recognition structures comprises a "correct" lattice, and wherein the second set of recognition structures comprises a "general" lattice.

Other features and advantages of various aspects and embodiments of the present invention will become apparent from the following description and from the claims.

BRIEF DESCRIPTION OF THE DRAWINGS

FIG. 12 illustrates a textual medical report generated based on a spoken report;

DETAILED DESCRIPTION

In one embodiment of the present invention, a system is provided for training an acoustic model for use in speech recognition. In particular, such a system may be used to perform training based on a spoken audio stream and a non-literal transcript of the spoken audio stream. Such a system may identify text in the non-literal transcript which represents concepts having multiple spoken forms. The system may attempt to identify the actual spoken form in the audio stream which produced the corresponding text in the non-literal transcript, and thereby produce a revised transcript which more accurately represents the spoken audio stream. The revised, and more accurate, transcript may be used to train the acoustic model, thereby producing a better acoustic model than that which would be produced using conventional techniques, which perform training based directly on the original non-literal transcript.

Figure 3:
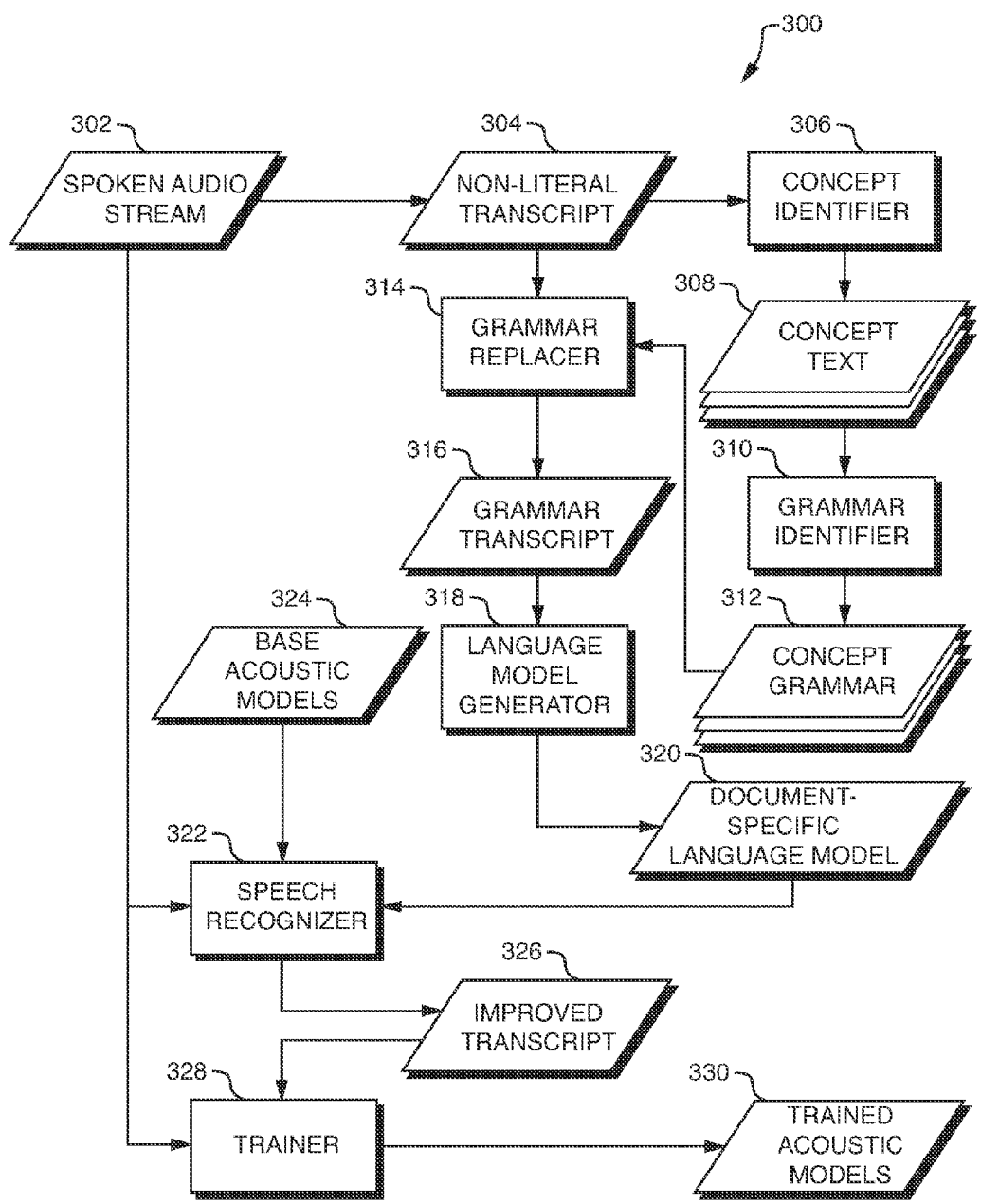
FIG. 3 is a dataflow diagram of a system for performing the method of FIG. 2 according to one embodiment of the present invention.

For example, referring to FIG. 3, a dataflow diagram is shown of a system 300 according to one embodiment of the present invention for training a set of acoustic models 330 based on a spoken audio stream 302 and a non-literal transcript 304 of the audio stream 302. The audio stream 302 may, for example, be a live or recorded spoken audio stream of a diagnosis and prognosis dictated by a doctor. The non-literal transcript 304 may, for example, be a textual report (such as the report 1200 shown in FIG. 12) generated based on the audio stream 302. The non-literal transcript 304 may, for example, be generated by a human transcriptionist, an automated transcription system, or a combination thereof.

Figure 1A:
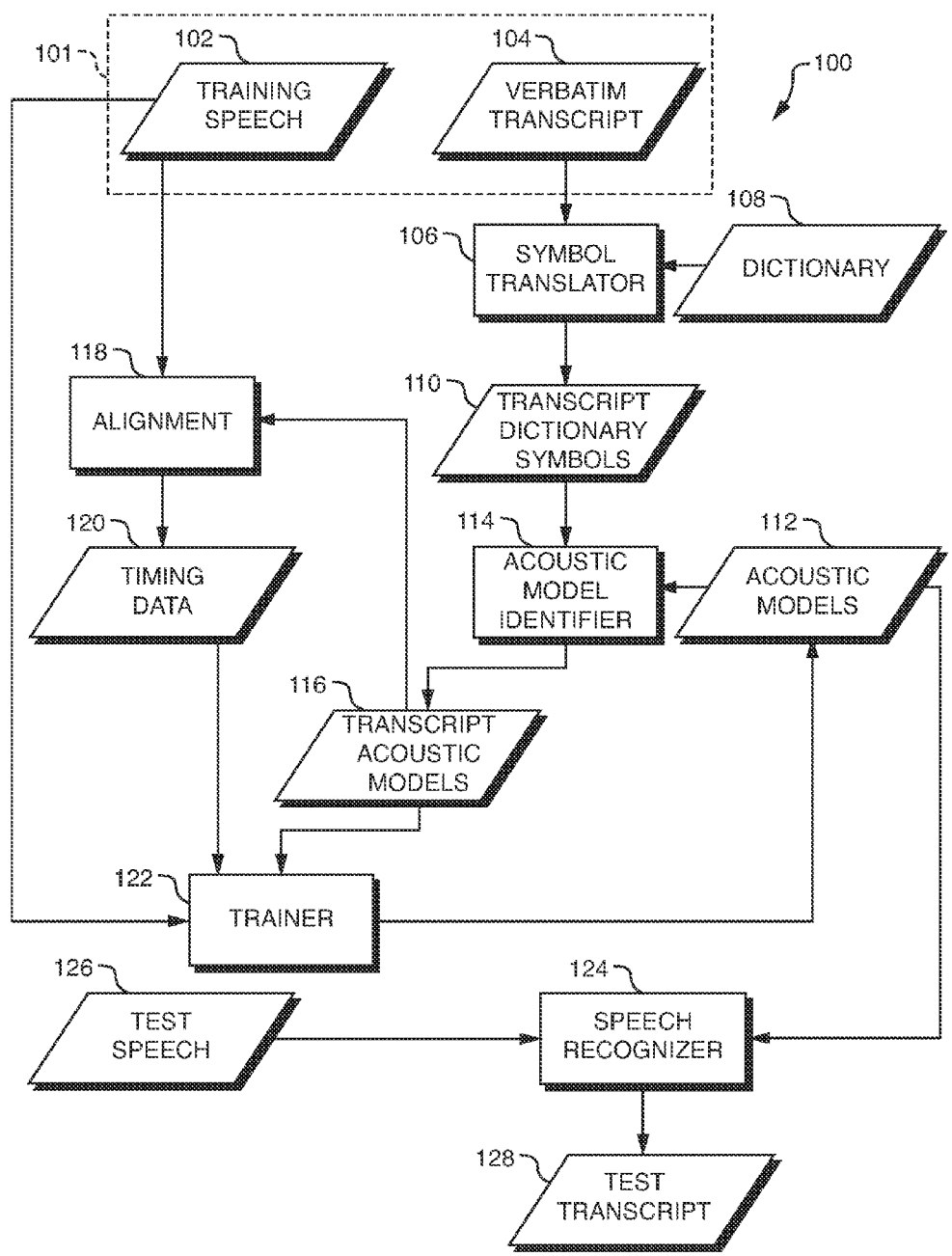
FIG. 1A is a dataflow diagram of a prior art system for training a set of acoustic models based on training speech and a corresponding verbatim transcript.
Figure 1B:
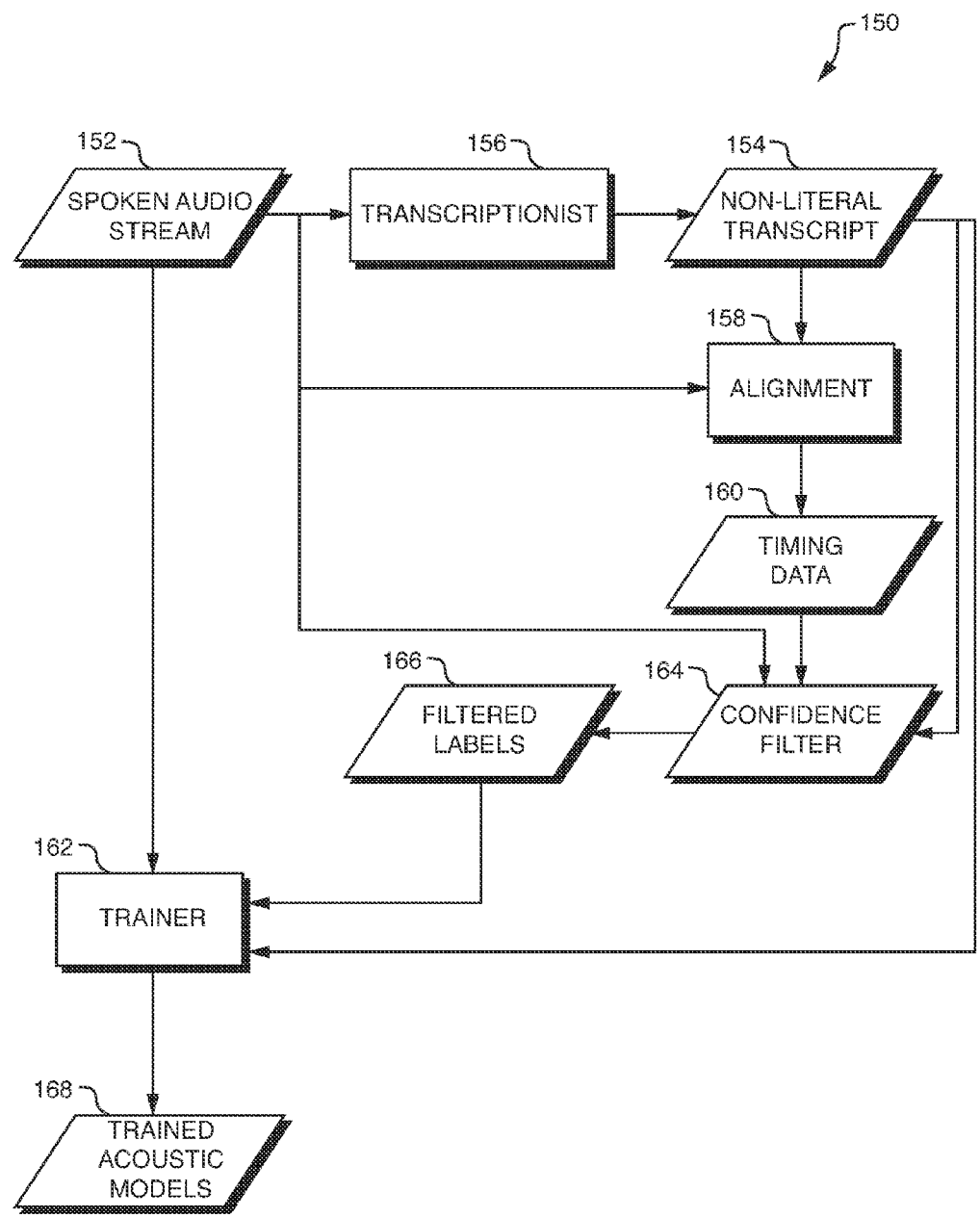
FIG. 1B is a dataflow diagram of a prior art system for training a set of acoustic models based on training speech and a corresponding non-literal transcript.
Figure 2:
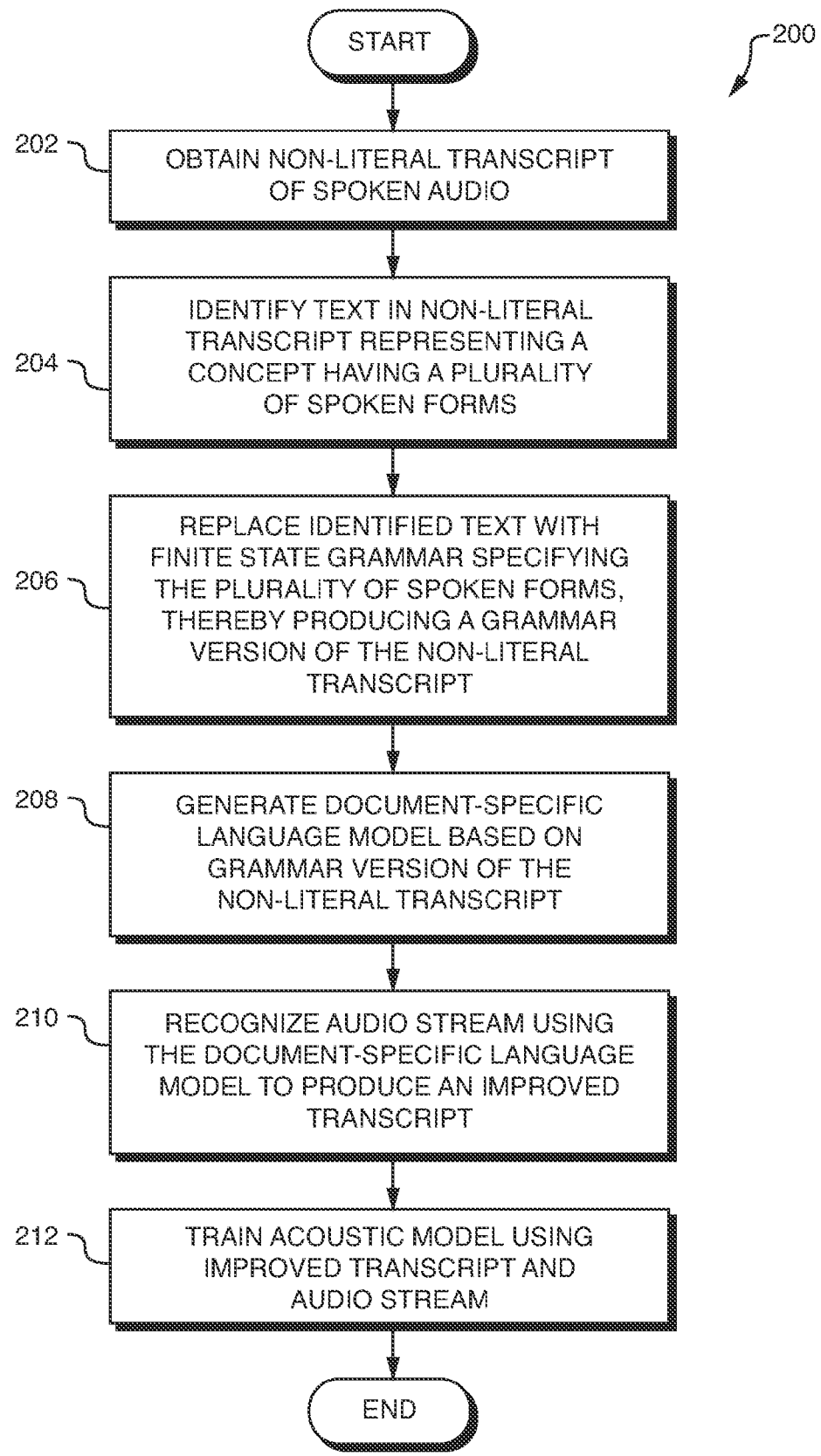
FIG. 2 is a flowchart of a method for training an acoustic model based on a spoken audio stream and a non-literal transcript of the audio stream according to one embodiment of the present invention.

Referring to FIG. 2, a flowchart is shown of a method 200 performed by the system 300 of FIG. 3 according to one embodiment of the present invention. The non-literal transcript 304 is obtained (step 202), such as by transcribing the audio stream 302. A concept identification unit 306 identifies text 308 in the non-literal transcript representing a concept having a plurality of spoken forms (step 204). Step 204 may be repeated multiple times to identify multiple instances of concept text 308, each representing a concept having a plurality of spoken forms.

The term "concept" as used herein includes, for example, semantic concepts (such as dates, times, numbers, codes, medications, medical history, diagnoses, and prescriptions) and syntactic concepts (such as phrases, sentences, paragraphs, sections, and the full document). A concept may be spoken in a plurality of ways. Each way of speaking a particular concept is referred to herein as a "spoken form" of the concept. Therefore, any semantic or syntactic content having a plurality of spoken forms is an example of a "concept" as that term is used herein. For example, a speaker may indicate the end of a sentence by saying "period", "next sentence", or "full stop". Therefore, the end of a sentence is an example of a "concept" as that term is used herein.

Consider, for example, the date Oct. 1, 1993, which is a semantic concept as that term is used herein. Spoken forms of this concept include the spoken phrases, "october first nineteen ninety three," "one october ninety three," and "ten dash one dash ninety three." Text such as "October 1, 1993" and "10/01/1993" are examples of "written forms" of this concept.

Now consider an example of a syntactic concept, such as the sentence "John Jones has pneumonia." This sentence, which is a concept as that term is used herein, may be spoken in a plurality of ways, such as the spoken phrases, "john jones has pneumonia," "patient jones diagnosis pneumonia," and "diagnosis pneumonia patient jones." The written sentence "John Jones has pneumonia" is an example of a "written form" of the same concept.

As yet another example, consider that there may be many ways to speak (or not to speak) a header for a particular section of a report. In the medical report 1200 (FIG. 12), for example, the section 1216 describing previous medications may be preceded by spoken phrases such as, "Previous medications include . . . ", "Prior meds are . . . ", or "Patient previously prescribed . . . " A human transcriptionist might, however, transcribe all of these alternative spoken forms into the section heading, "Meds:". When the transcriptionist encounters the prior medication information in the audio stream 302, the transcriptionist may insert such information into the previous medications section 1216 after the introductory text "Meds:".

Now consider a document, such as the non-literal transcript 304, which contains a particular written form of a particular concept. Assume, for example, that the transcript 304 contains the text "10/01/1993." There is no way to know, a priori, which spoken form was spoken by the speaker of the audio stream 302 to produce the text "10/01/1993." Although the speaker may, for example, have spoken the phrase "ten dash oh one dash nineteen ninety three," which may have been transcribed literally as "10/01/1993", the speaker may alternatively have spoken the phrase "october first ninety three," "first october ninety three," or any other spoken form of the same concept. The transcriptionist may have produced the written form "10/01/1993" from any of the spoken forms because, for example, such a written form is required by a particular written report format. The non-literal transcript 304, therefore, does not necessarily include information about the spoken forms of concepts in the spoken audio stream 302 which correspond to the written forms of the same concepts in the non-literal transcript 304.

As described above, however, it is desirable to obtain a verbatim transcript of the spoken audio stream 302 for use in training the acoustic model 330. As further described above, however, it may be prohibitively difficult or expensive to generate such a verbatim transcript from scratch. As will be described in more detail below, this problem is addressed in various embodiments of the present invention by using alternative spoken forms of the concept(s) identified by the concept identifier 306 as hints to a speech recognizer 322, which recognizes the spoken audio stream 302 and creates a improved transcript 326 which is intended to more closely represent a verbatim transcript of the audio stream 302 than the original non-literal transcript 304. The improved transcript 326 may then be provided to a trainer 328 to produce the acoustic models 330, thereby improving the quality of the acoustic models 330.

More specifically, in the embodiment illustrated in FIGS. 2 and 3, the concept identifier 306 identifies text 308 representing a concept which has a plurality of spoken forms. The concept identifier 306 need not, however, identify the plurality of spoken forms. The concept identifier 306 may identify the concept text 308 (step 204) in any of a variety of ways. The concept identifier 306 may, for example, be configured to recognize text formats (i.e., patterns) which are likely to represent concepts having multiple spoken forms. For example, the concept identifier 306 may be configured to identify text having the format "DD/MM/YYYY" (e.g., "01/10/1993"), "MM/DD/YYYY" (e.g., "10/01/1993"), "MMM DD, YYYY" (e.g., "Oct 01, 1993"), or "DD MMM YYYY" (e.g., "01 Oct 1993") as text representing a date. The concept identifier 306 may similarly be configured to recognize written forms which represent alternative spoken forms of other kinds of concepts, such as numbers, diagnoses, and medications.

In the case of a syntactic concept such as the previous medications section 1214, the concept identifier 306 may be configured to recognize any of a predetermined set of written forms (such as "Meds:" or "Medications") as indicating the onset of the previous medications section 1214.

The concept identifier 306 may indicate the concept text 308 in any of a variety of ways. In general, the concept identifier 306 marks the concept text 308 with a name or other unique identifier of the corresponding concept. In one embodiment of the present invention, for example, the concept identifier 306 inserts markup into the non-literal transcript 304 which delimits the concept text 308. The non-literal transcript 304 may, for example, be represented in the Extensible Markup Language (XML), and the markup may be represented using XML tags. For example, the text "10/01/1993" may be marked up as follows: "<DATE>10/01/1993</DATE>". The start tag "<DATE>" and corresponding end tag "</DATE>" delimit the date concept text "10/01/1993". The text may be further marked up, such as by marking up the month, day, and year, as in <DATE><MONTH>10</MONTH><DAY>01</DAY><YEAR>1993</YEAR></DATE>. As an example of a syntactic concept, the text "FamHx: Reviewed." may be marked up as follows: "<FAM HISTORY>Reviewed.</FAM HISTORY>".

Note that the use of a markup language such as XML, however, is merely one example of a way in which the concept identifier 306 may indicate the concept text 308, and does not constitute a limitation of the present invention.

The identified concept text 308 in the non-literal transcript 304 is replaced with a finite state grammar 312 which specifies a plurality of spoken forms of the concept, thereby producing a document 316 that is referred to here as the "grammar version" of the transcript 304 (step 206). In general, a finite state grammar specifies a plurality of spoken forms for a concept and associates probabilities with each of the spoken forms. For example, a finite state grammar for the date Oct. 1, 1993, might include the spoken form "october first nineteen ninety three" with a probability of 0.7, the spoken form "ten one ninety three" with a probability of 0.2, and the spoken form "first october ninety three" with a probability of 0.1. The probability associated with each spoken form is an estimated probability that the concept will be spoken in that spoken form in a particular audio stream. A finite state grammar, therefore, is one kind of probabilistic language model. The term "probabilistic language model," as used herein, refers to any language model which assigns probabilities to sequences of spoken words. Examples of techniques that may be used to generate finite state grammars in accordance with embodiments of the present invention will be described in more detail below.

To perform step 206, a grammar identifier 310 identifies the finite state grammar 312 (referred to in FIG. 3 as a "concept grammar"), which specifies a plurality of spoken forms of the concept represented by the concept text 308. Examples of techniques that may be used by the grammar identifier 310 to identify the concept grammar 312 will be described in more detail below.

A grammar replacer 314 replaces the concept text 308 in the non-literal transcript 304 with the concept grammar 312, thereby producing the grammar form 316 of the transcript 304. The grammar form 316 of the transcript 304, therefore, may include both "flat" text (i.e., text which need not be represented as a finite state grammar) and finite state grammars (e.g., the concept grammar 312). Note that step 206 may be repeated for each of a plurality of concepts having corresponding concept texts and concept grammars, in which case the grammar replacer 314 may replace a plurality of concept texts 308 in the non-literal transcript 304 with a plurality of corresponding concept grammars 312.

Note further that since concepts may range from low-level concepts spanning a few words (such as a date concept) to high-level concepts spanning a paragraph, section, or even the entire document, the grammar replacer 314 may replace any amount of text with a corresponding grammar, up to and including the entire document. In general, a grammar representing an entire document may represent, for example, alternative sequences in which sections of the document may be spoken. Techniques for implementing such a global document grammar are described in more detail, for example, in the above-referenced patent application entitled "Automated Extraction of Semantic Content and Generation of a Structured Document from Speech." As further described in that patent application, the global document grammar may be hierarchical. For example, the global document grammar may contain a root node having child nodes representing the sections of the document. Each such child node may have further child nodes, which may represent concepts (such as sub-sections or dates) that may appear within the document sections. Therefore it should be appreciated that steps 204-206 may be implemented to recursively replace text in the non-literal transcript 304 with grammars having a structure that corresponds to the structure of the global document grammar.

Consider again the simple example in which the non-literal transcript 304 includes the text "when compared to previous film from <DATE>October 1, 1993</DATE>". Let the text "[GRAMMAR(DATE(10/1/1993))]" represent a finite state grammar for the date Oct. 1, 1993. Such a finite state grammar includes a plurality of spoken forms for that date and corresponding probabilities. After step 206, the grammar form of the non-literal transcript 304 may therefore be represented as "when compared to previous film from [GRAMMAR(DATE (10/1/1993))]". From this example it can be seen that the grammar form 316 of the non-literal transcript 304 may include both flat text (e.g., "this is doctor smith on") and a finite state grammar (i.e., GRAMMAR(DATE(10/1/1993))) or a reference to such a grammar.

A language model generator 318 generates a language model 320 based on the grammar version 316 of the transcript 304 (step 208). The language model 320 is referred to herein as a "document-specific" language model because it includes probabilities of word occurrences which reflect the frequencies of such occurrences in the document 316. The document-specific language model 320 may, for example, be a conventional n-gram language model. Examples of techniques that may be used to generate the document-specific language model 320 will be described in more detail below.

A speech recognizer 322 uses the document-specific language model 320 to recognize the spoken audio stream 302 and thereby to produce an improved transcript 326 (step 210). For reasons which will be described below, the improved transcript 326 will typically be a more accurate transcript of the spoken audio stream 302 than the non-literal transcript 304.

In general, a speech recognizer typically uses both a language model and an acoustic model to perform speech recognition. Referring again to FIG. 3, the speech recognizer 322 may be a conventional speech recognizer which uses a base acoustic model 324 as an acoustic model and uses the document-specific language model 320 as a language model to recognize the spoken audio stream 302 and thereby to produce the improved transcript 326. As will be described in more detail below, the speech recognizer 322 may interpolate the document-specific language model 320 with another language model to produce improved recognition results.

A trainer 328 trains the acoustic models 330 based on the improved transcript 326 and the spoken audio stream 302 using conventional training techniques (step 212). Because the transcript 326 more closely represents a verbatim transcript of the audio stream 302 than the non-literal transcript 304, the quality of the acoustic model 330 is higher than if the non-literal transcript 304 had been used to train the acoustic model 330. Experimental results have indicated that improvements in accuracy of 10-20% may be obtained using the techniques disclosed herein relative to a baseline in which training is performed using conventional non-literal transcripts.

It was stated above that the grammar identifier 310 may identify concept grammar 312, which includes: (1) a plurality of spoken forms of the concept represented by concept text 308, and (2) a plurality of corresponding probabilities. Examples of techniques will now be described for identifying the concept grammar 312.

Figure 4:
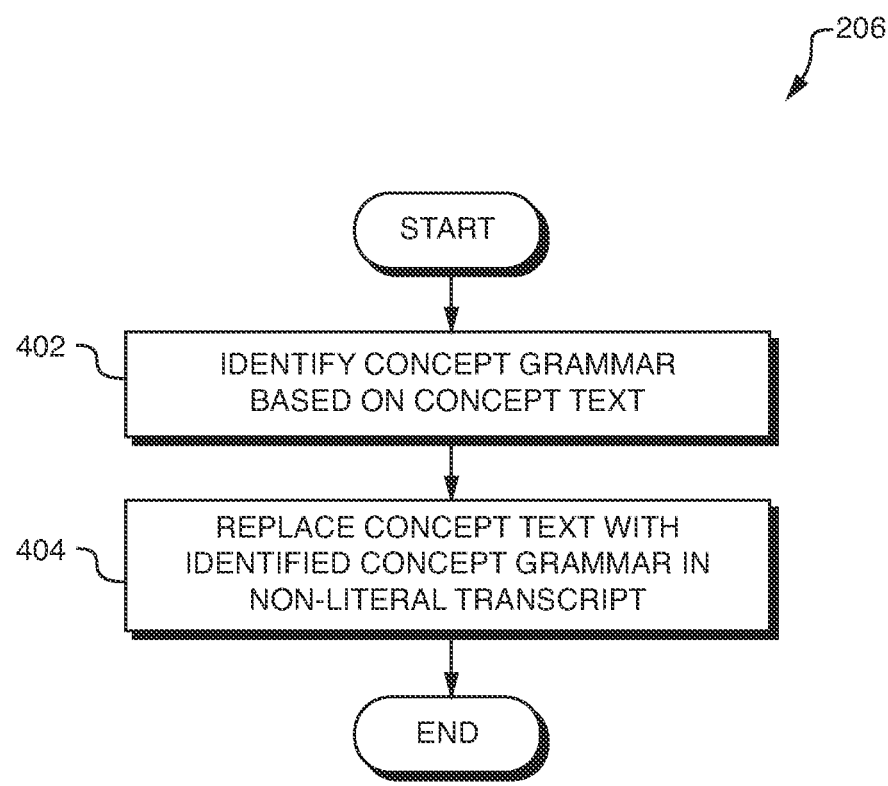
FIG. 4 is a flowchart of a method that is used to replace text in the non-literal transcript of FIG. 3 with a finite state grammar according to one embodiment of the present invention.

Referring to FIG. 4, a flowchart is shown of a method that is used to replace the concept text 308 in the non-literal transcript 304 with the concept grammar 312 (FIG. 2, step 206) in one embodiment of the present invention. The concept grammar 312 is identified (step 402). As described above, step 402 may be performed by the grammar identifier 310. The concept text 308 in the non-literal transcript 304 is replaced with the concept grammar 312 (step 404). As described above, step 404 may be performed by the grammar replacer 314.

Figure 5:
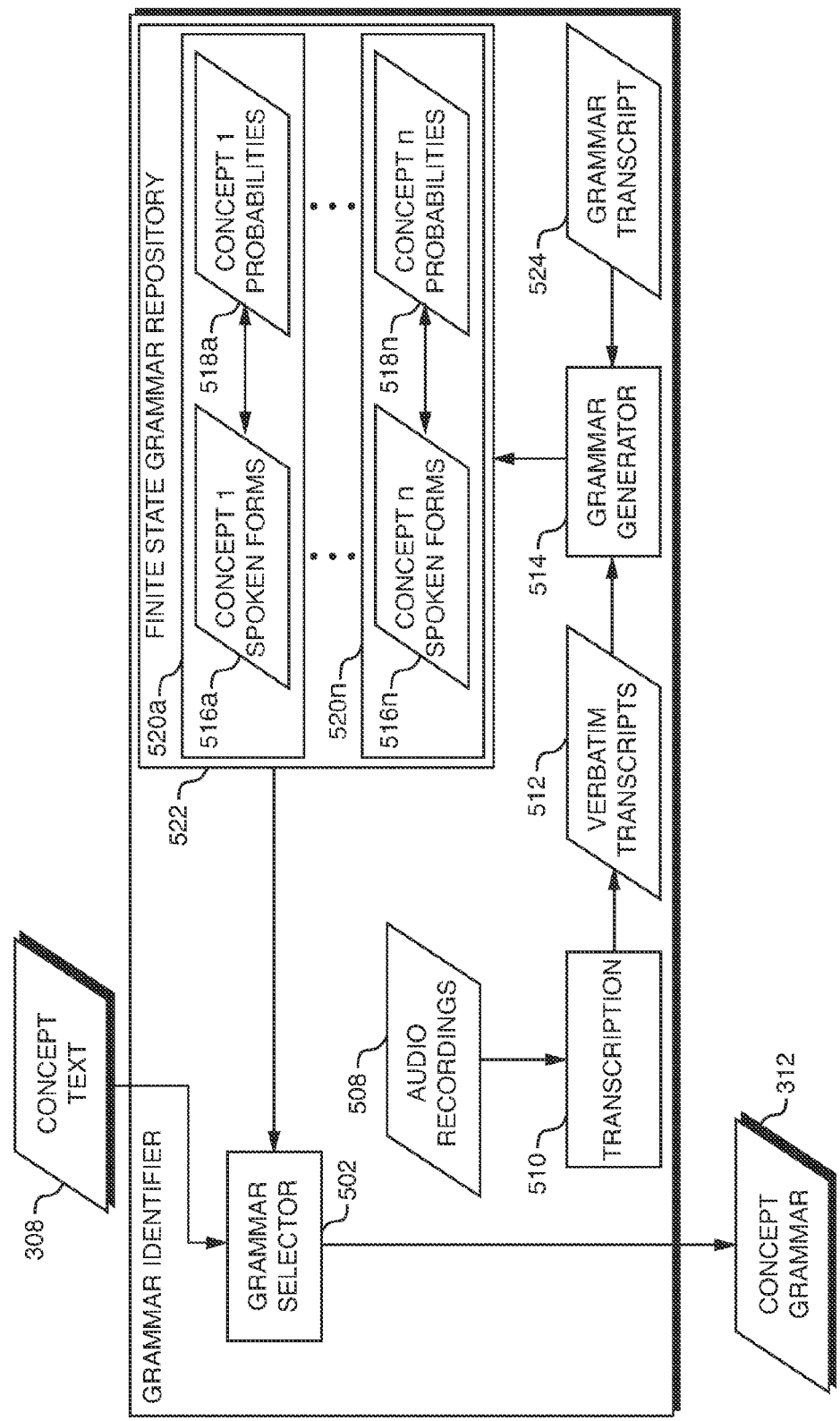
FIG. 5 is a dataflow diagram which illustrates techniques for identifying a finite state grammar for use in the system of FIG. 3 according to one embodiment of the present invention.

Referring to FIG. 5, a dataflow diagram is shown which illustrates the grammar identifier 310 in more detail according to one embodiment of the present invention. The grammar identifier 310 includes a repository 522 of finite state grammars 520*a*-*n*. Each of the grammars 520*a*-*n* corresponds to a different concept. For example, spoken forms 516*a* may be alternative spoken forms for a "date" concept, while spoken forms 516*n* may be alternative spoken forms for a "section" concept.

The grammars 520*a*-*n* include spoken forms 516*a*-*n* for the corresponding concepts. The spoken forms 516*a*-*n* are paired with probabilities 518*a* of occurrence of those spoken forms. Prior to performance of the method illustrated in FIG. 4, the grammar repository 522 may be generated by a finite state grammar generator 514 as follows. A set of baseline ("seed") grammars are generated manually and used to populate the finite state grammar repository 522. For example, a grammar for the header to the patient medical history section 1214 (FIG. 12) may include the spoken forms "clinical history is," "previous medical history," and "history is," based on the system designer's knowledge or belief that such spoken forms may be used to introduce the patient medical history section 1214.

The grammar identifier 310 may include or otherwise have access to a set of audio recordings 508, such as audio recordings of other speech in the same domain as the audio recording 302, and/or other speech by the speaker whose speech is recorded in the audio recording 302. The grammar identifier 310 also includes or otherwise has access to a set of verbatim transcripts 512 of the audio recordings 508. The verbatim transcripts 512 may be generated, for example, by transcribing 510 the audio recordings 508 or by using the techniques described above with respect to FIG. 3.

A grammar transcript 524 may be generated from the non-literal transcript 304 based on the set of baseline grammars, using the techniques described above with respect to FIG. 3 for generating the grammar transcript 316. The verbatim transcripts 512 may then be parsed against the grammar transcript 524 using, for example, the filtering techniques described below with respect to FIG. 11. The finite state grammar generator 514 may use the results of such parsing to identify the frequencies with which spoken forms in the baseline grammars appear in the verbatim transcripts. The finite state grammar generator 514 may use such frequencies as initial probabilities for each of the spoken forms in the grammars 520*a*-*n* in the grammar repository 522. Furthermore, any mismatches between text in the verbatim transcripts 512 and spoken forms in the grammar repository 522 may be flagged and used to improve the grammar repository (such as by added new spoken forms to the grammars 520*a*-*n*), as described in more detail below with respect to FIG. 11.

For example, the finite state grammar generator 514 may ascertain that 90% of the dates in the verbatim transcripts 512 appear in the form "MM/DD/YY" (e.g., "ten slash one slash ninety-three") and that 10% of the dates appear in the form "MMM D YYYY" (e.g., "october one nineteen ninety three"). The finite state grammar generator 514 may use these relative frequencies as the probabilities 518*a*, assuming that grammar 520*a* is a "date" grammar.

The grammar identifier 310 includes a grammar selector 502 which identifies the name of the concept tagged in the concept text 308, uses the identified concept name to identify the corresponding grammar in the grammar repository, extracts the identified grammar from the grammar repository 522, and provides the extracted grammar as the concept grammar 312.

Note that although in the example illustrated in FIG. 5, a single concept grammar 312 is selected for a single instance of concept text 308 representing a single concept, in practice the grammar identifier 310 may analyze the entire non-literal transcript 304 and all instances of concept text 308 within it in a single pass to identify the corresponding grammars more efficiently.

It was stated above with respect to FIGS. 2 and 3 that the grammar version 316 of transcript 304 is provided to the language model generator 318. The language model generator 318 need not, however, generate the language model 320 based directly or solely on the grammar version 316 of transcript 304. For example, in one embodiment of the present invention, the grammar version 316 of transcript 304 is normalized before being provided to the language model generator 318.

Figure 6:
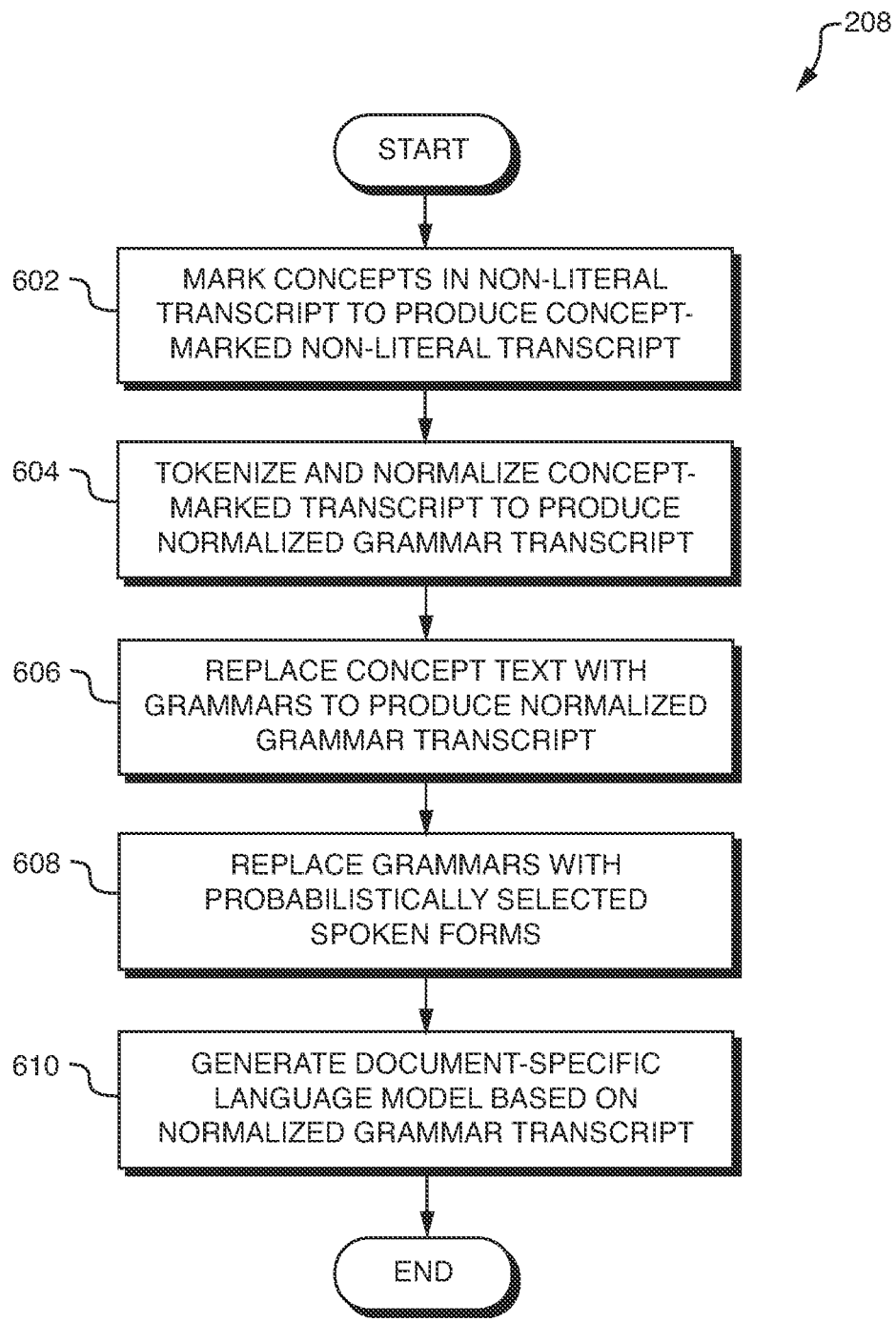
FIG. 6 is a flowchart of a method that is used in one embodiment of the present invention to generate the document-specific language model of FIG. 3 according to one embodiment of the present invention.
Figure 7:
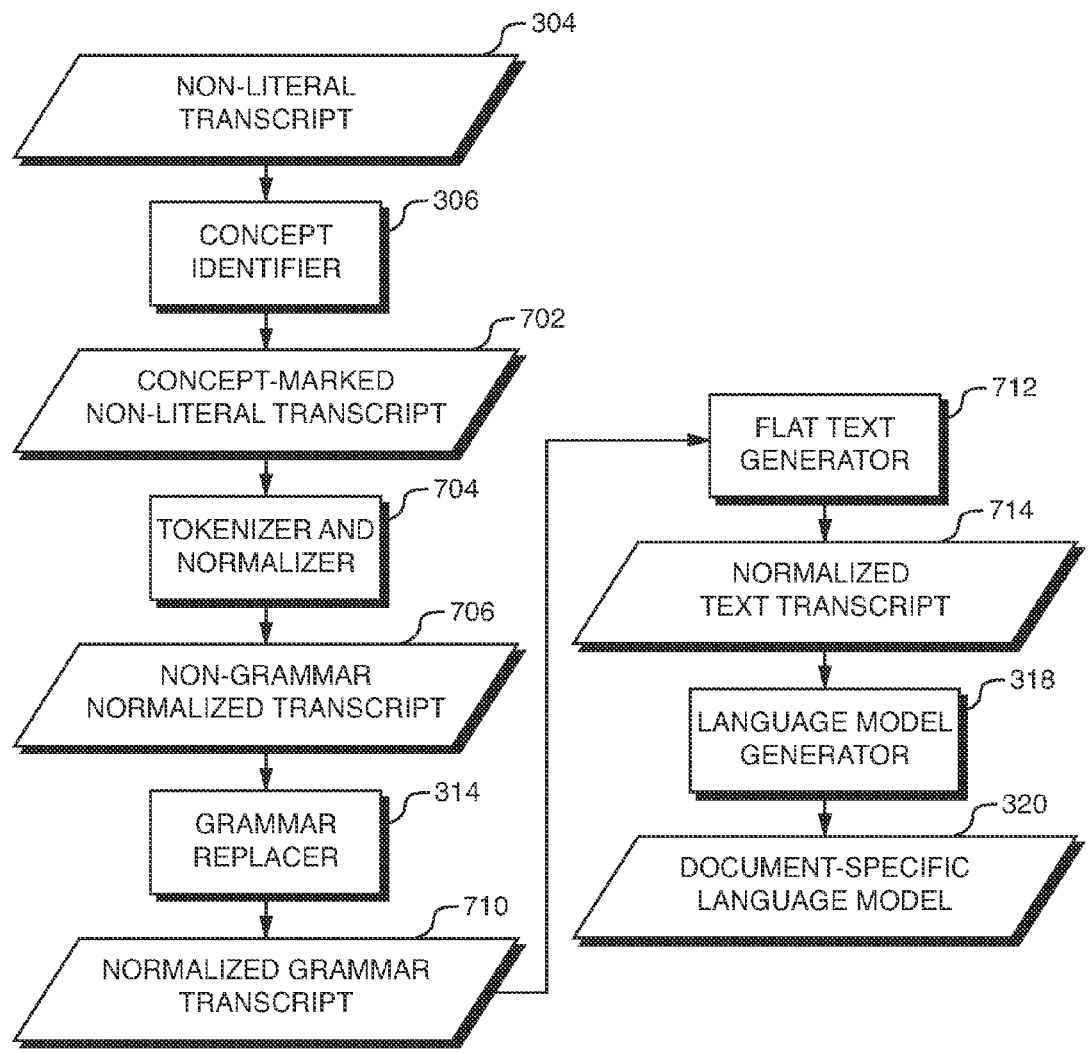
FIG. 7 is a dataflow diagram of an alternative embodiment of a portion of the system of FIG. 3 which performs the method illustrated in FIG. 6 according to one embodiment of the present invention.

Referring to FIG. 6, a flowchart is shown of a method that is used in one embodiment of the present invention to generate the document-specific language model 320 (FIG. 2, step 208) based on a normalized version of the grammar version 316 of transcript 304. Referring to FIG. 7, a dataflow diagram is shown of an alternative embodiment of a portion of the system 300 (FIG. 3) which may perform the method illustrated in FIG. 6.

In the embodiment illustrated in FIG. 7, the system 300 includes a tokenizer and normalizer 704. The term "tokenization" refers to segmenting text into consistent words (tokens). The term "normalization" refers to replacing text with its canonical form. Various kinds of tokenization techniques are well-known to those having ordinary skill in the art, such as splitting punctuation marks (e.g., periods and commas) from the words immediately preceding them. Various kinds of normalization are well-known to those having ordinary skill in the art, such as changing the case of all words to lowercase, changing punctuation marks into textual representations their spoken forms (e.g., changing "." to "% period %"), and changing blank lines to the text "% new paragraph %". For example, the words "the", "The", and "THE" may be normalized by converting all of them into the canonical form "the". In general, normalization is used to convert an existing transcript into a form which more closely resembles a verbatim transcript of the same speech.

Conventional normalization techniques have been applied to documents consisting of plain text. In embodiments of the present invention, however, the grammar version 316 of transcript 304 may include both plain text and finite state grammars. In one embodiment of the present invention, normalization and creation of the grammar version 316 of transcript 304 proceeds in multiple steps. First, the concept identifier 306 marks up, or otherwise modifies, the non-literal transcript 304 to indicate any identified concepts, thereby producing a concept-marked non-literal transcript 702 (step 602). Plain text in the concept-marked non-literal transcript 702 is normalized by tokenizer/normalizer 704, such as by using conventional tokenization and normalization techniques (step 604). The resulting document 706 is referred to herein as a non-grammar normalized transcript for reasons that will become clear based on the description below. Marked concepts in the concept-marked transcript 702 remain unchanged in the non-grammar normalized transcript 706.

The grammar replacer 314 and/or grammar identifier 310 replaces marked-up concept text in the non-grammar normalized transcript 706 with corresponding grammars to produce a normalized grammar transcript 710 (step 606). The resulting normalized transcript 710, therefore, differs from a conventional normalized document in that it includes both plain text and finite state grammars.

In one embodiment, a flat text generator 712 replaces each grammar in the normalized grammar transcript 710 with all of its spoken forms, weighted by their associated probabilities, to produce a normalized text transcript 714 which includes flat text and no finite state grammars (step 608). Alternatively, the flat text generator 712 may, for example, replace each grammar in the normalized grammar transcript 710 with its highest-probability spoken form, or with a randomly-selected one of its spoken forms.

The language model generator 318 then generates the document-specific language model 320 based on the normalized text transcript 714 (step 610), rather than based directly on the grammar version 316 of transcript 304, as described above with respect to FIGS. 2-3. Techniques for generating a language model based on a grammar are well-known to those of ordinary skill in the art. The resulting language model 320 may be an n-gram language model having the same structure as any other conventional n-gram language model, including class language models.

It was stated above with respect to the embodiments illustrated in FIGS. 2 and 3 that the speech recognizer 322 recognizes the audio stream 302, and thereby produces the improved transcript 326, using the base acoustic model 324 and the document-specific language model 320. Techniques that may be used by the speech recognizer 322 to generate the improved transcript 326 according to various embodiments of the present invention will now be described in more detail.

Figure 8:
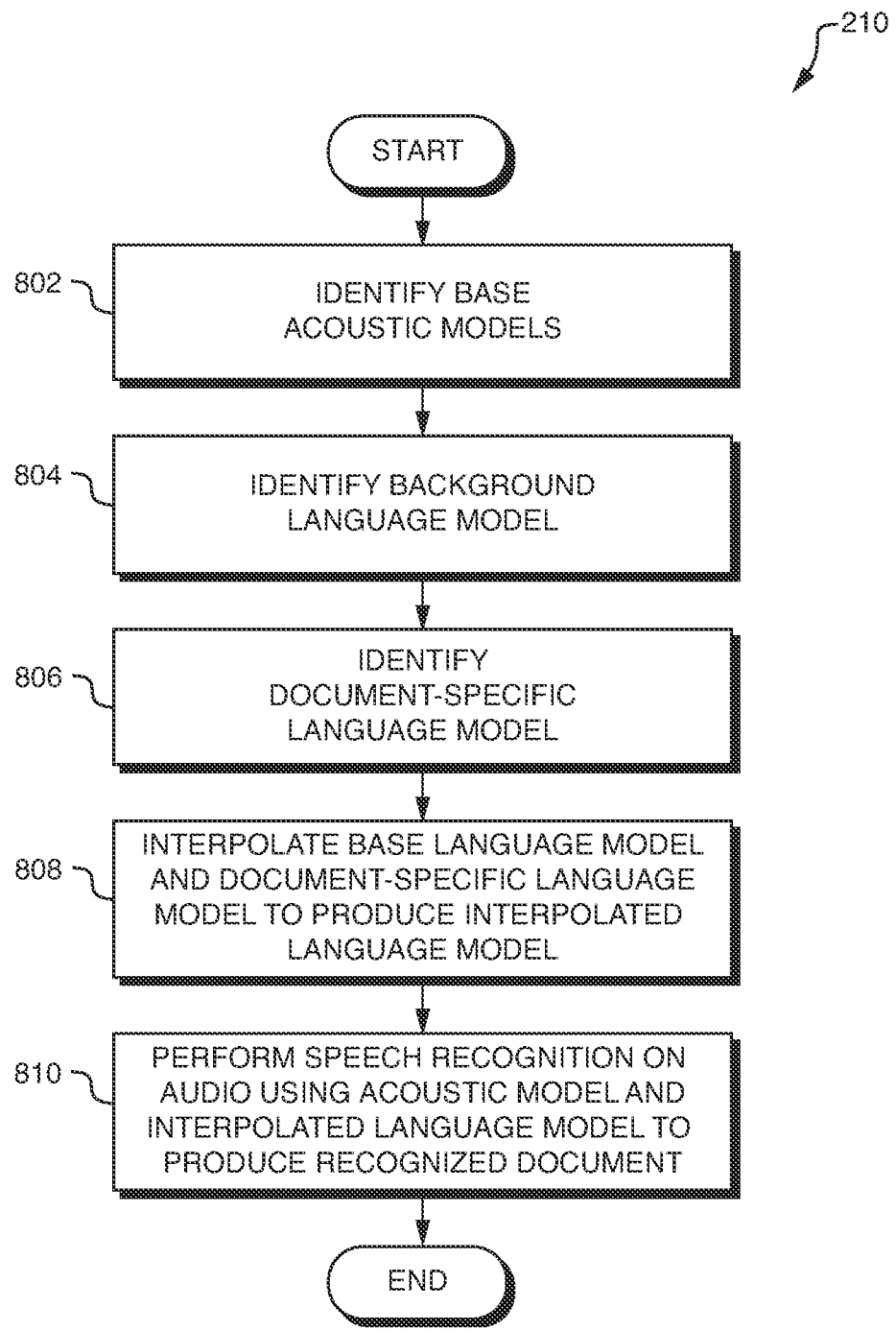
FIG. 8 is a flowchart of a method that is used in one embodiment of the present invention to recognize the audio stream of FIG. 3 and thereby to produce a document representing the audio stream.
Figure 9:
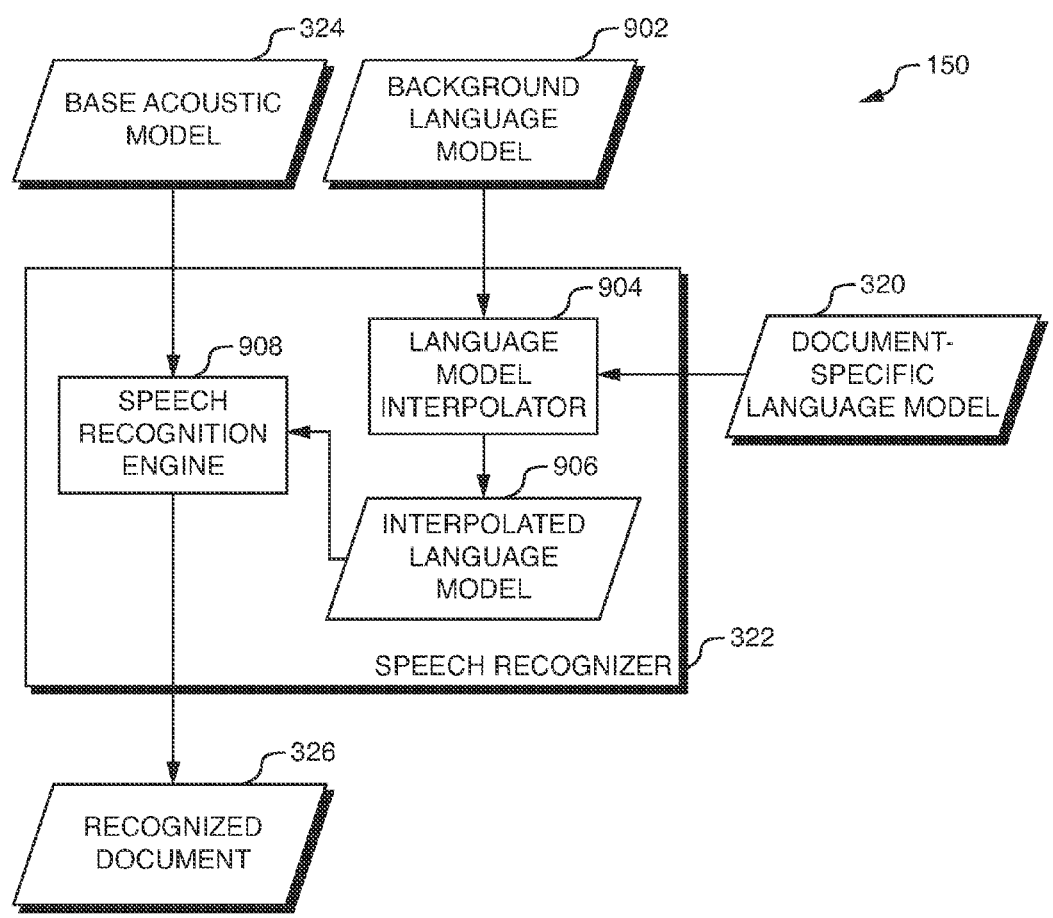
FIG. 9 is a dataflow diagram of an alternative embodiment of a portion of the system of FIG. 3 which performs the method of FIG. 8 in one embodiment of the present invention.

Referring to FIG. 8, a flowchart is shown of a method that is used in one embodiment of the present invention to recognize the audio stream 302 and thereby to generate the improved transcript 326 (FIG. 2, step 210). Referring to FIG. 9, a dataflow diagram is shown of an alternative embodiment of a portion of the system 300 (FIG. 3) which may perform the method illustrated in FIG. 8.

The speech recognizer 322 identifies the base acoustic model 324 (step 802). The base acoustic model 324 may be any acoustic model 324, such as an acoustic model generated based on the speech of the speaker who spoke the audio stream 302, or based on a variety of speakers speaking the same language as the speaker of the audio stream 302. The base acoustic model 324 may or may not be generated based on speech in the same domain as the audio stream 302.

In the embodiment illustrated in FIG. 9, the system 300 also includes a background language model 902. The background language model 902 may, for example, be generated based on a large number of documents in the same domain as the audio stream 302, whether or not such documents have corresponding audio streams. Such documents may have the same form as the normalized grammar transcript 710, i.e., they may include both normalized plain text and finite state grammars. The probabilities in the background language model 902 may be based on the frequencies of occurrence of word sequences and of spoken forms in the finite state grammars.

The background language model 902 may cover spoken audio data containing phrases not contained in the non-literal transcript 304 and which therefore are not covered by the document-specific language model 320. Therefore, in one embodiment of the present invention, the speech recognizer 322 includes a language model interpolator 904 which identifies the background language model 902 (step 804) and the document-specific language model 320 (step 806), and interpolates the two language models 902 and 320 to produce an interpolated language model 906 that has better coverage than either the background language model 902 or the document-specific language model 320 standing alone (step 808).

The language model interpolator 904 may use any of a variety of well-known interpolation techniques to produce the interpolated language model 906. In particular, the language model interpolator 904 may weight the document-specific language model 320 more heavily than the background language model 902 in the interpolation process, using well-known techniques.

The speech recognizer 322 includes a speech recognition engine 908 which performs speech recognition on the audio stream 302, using the base acoustic model 324 as its acoustic model and the interpolated language model 906 as its language model, thereby producing the improved transcript 326 (step 810). The effect of using the interpolated language model 906 in the speech recognition process is that the grammar version 316 of transcript 304, reflected in the document-specific language model 320, serves as an additional constraint on the background language model 902 and thereby assists in improving the accuracy of the improved transcript 326.

Although the improved transcript 326 is expected to more closely represent a verbatim transcript of the audio stream 302 than the original non-literal transcript 304, the improved transcript 326 may contain errors. Therefore, in one embodiment of the present invention, apparent errors in the improved transcript 326 are identified and removed from the improved transcript 326 prior to using the improved transcript 326 for training. As a result, the quality of training may be improved.

Figure 10:
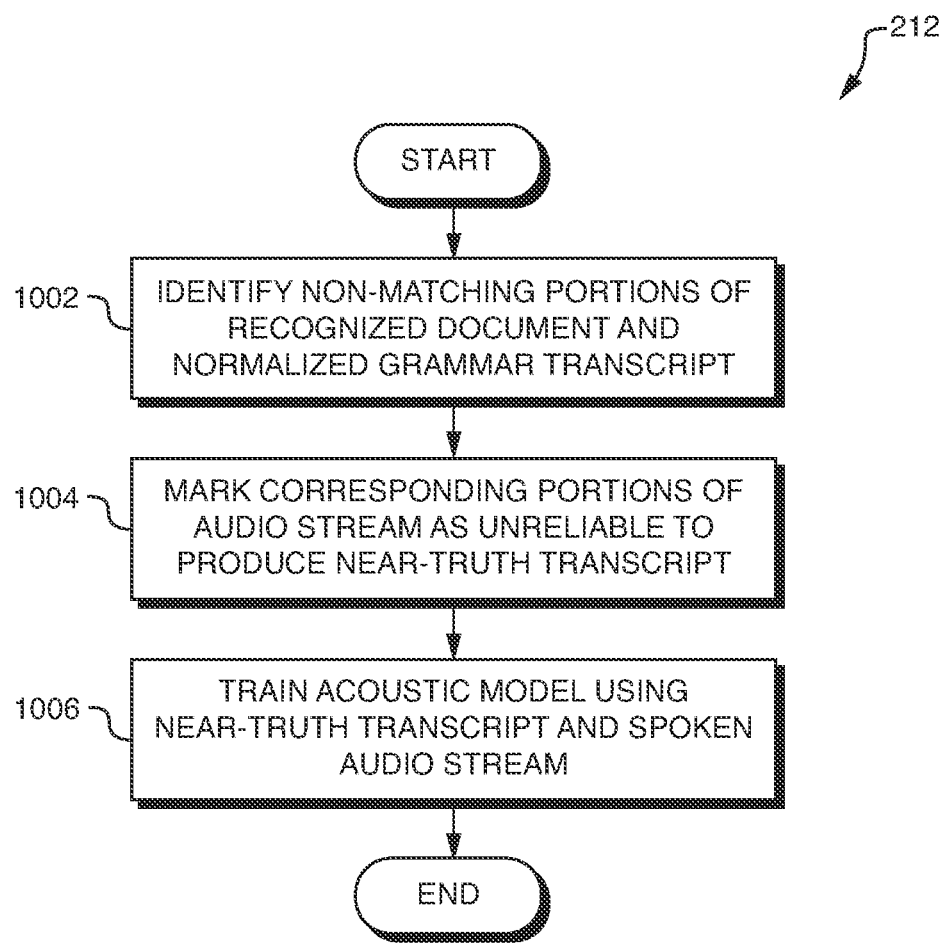
FIG. 10 is a flowchart of a method that is used in one embodiment of the present invention to train the acoustic model of FIG. 3.
Figure 11:
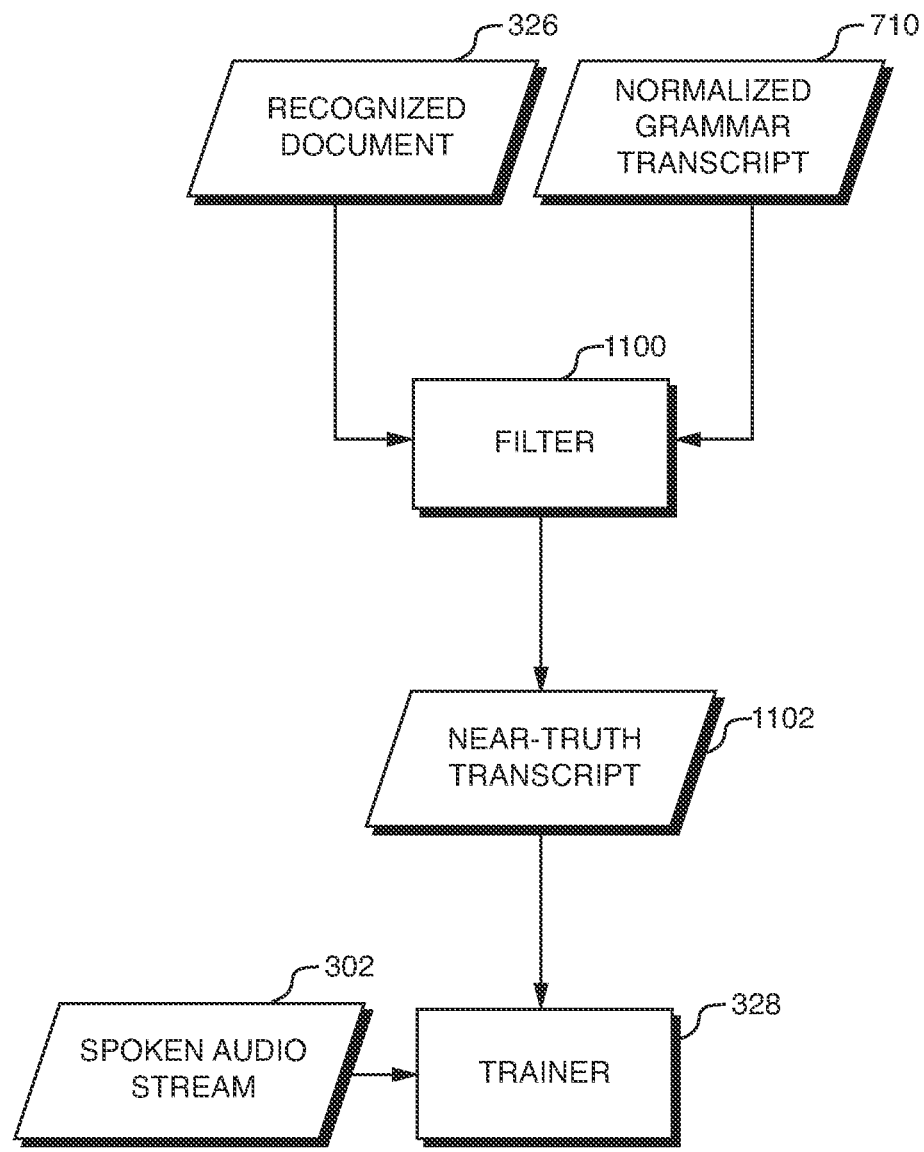
FIG. 11 is a dataflow diagram of an alternative embodiment of a portion of the system of FIG. 3 which performs the method of FIG. 10 in one embodiment of the present invention.

Referring to FIG. 10, a flowchart is shown of a method that is used in one embodiment of the present invention to train the acoustic model 330 (step 212) using a filtered version of the improved transcript 326 to improve the results of training. Referring to FIG. 11, a dataflow diagram is shown of an alternative embodiment of a portion of the system 300 (FIG. 3) which may perform the method illustrated in FIG. 10.

In the embodiment illustrated in FIG. 11, the system 300 includes a filter 1100. The filter 1100 identifies non-matching portions of the improved transcript 326 and the normalized grammar transcript 710 (step 1002), and indicates in the transcript 710 that the corresponding sections of the spoken audio stream 302 are unreliable and therefore should not be used for training. The resulting transcript 1102, in which unreliable portions of the audio stream 302 are flagged, is referred to herein as a near-truth transcript 1102 (step 1004). The flagging of the unreliable portions of the audio stream is critical to the success of some training methods, such as discriminative training, which rely very heavily on the "correctness" of the transcript.

The filter 1100 may perform filtering (steps 1002 and 1004) in any of a variety of ways. For example, in one embodiment of the present invention, the filter 1100 is a robust parser which may be implemented using any of a variety of techniques well-known to those having ordinary skill in the art. A robust parser is capable of parsing a text (such as a recognized transcript) against a grammar to determine whether the text is consistent with the grammar. A robust parser is "robust" in the sense that it is capable of identifying portions of the text and grammar as matching each other even if the two portions do not align precisely with each other. For example, a robust parser may compare the text "Previous medications include" and "Previous medications of the patient include" and determine that the second sentence is the same as the first, with the addition of the inserted text ("of the patient"). Robust parsers may also recognize matching text in two documents despite other kinds of differences, such as text deletions and substitutions.

When a robust parser detects a difference between a first document and a second document, the parser may mark up the first document to indicate the differences between it and the second document. In the example above, a robust parser might mark up the first sentence as follows: "Previous medications <INSERT> of the patient</INSERT> include". The robust parser thereby indicates that the second sentence is the same as the first sentence, with the exception of the specified inserted text.

The preceding discussion describes comparisons made by the filter between plain text in the improved transcript 326 and the normalized grammar transcript 710. Recall, however, that the normalized grammar transcript 710 may also include finite state grammars. When the robust parser encounters a grammar in the transcript 710, the parser may attempt to match text in the improved transcript 326 with any of the alternative spoken forms in the grammar. If a match is found, the robust parser may treat the text in the improved transcript 326 as matching the grammar in the transcript 710. If no match is found, the parser may treat this as a mismatch in the same way as if two units of plain text had mismatched.

In the embodiment illustrated in FIGS. 10 and 11, training is performed on the acoustic model 330 using the near-truth transcript 1102 and the audio stream 302 (step 1006), rather than using the improved transcript 326 directly, as illustrated in FIG. 3. The use of a robust parser may enable a larger amount of the improved transcript 326 to be retained in the near-truth transcript 1102 than if a simple character-by-character or word-by-word comparison were employed. Because the quality of training increases with the amount of valid training data, the use of a robust parser may thereby increase training quality.

Acoustic models may be trained using various techniques, such as maximum likelihood optimization and discriminative training, or any combination thereof. Discriminative training techniques are preferred due to their potential for improving overall speech recognition accuracy. However, discriminative training techniques that use information from potential misrecognition or near miss recognition to adjust the models to optimize recognition depend on the availability of large amounts of data and corresponding verbatim transcripts. Such techniques determine whether input speech has been recognized correctly by comparing the hypothesis from the recognizer to a verbatim transcription of the same input speech. Such a process, therefore, usually requires verbatim transcriptions of the training data. Using non-verbatim transcripts with such techniques risks mis-training the models.

For example, if a speaker says " . . . past medical history . . . " and the system recognizes " . . . has medical history . . . ", discriminative training methods would adjust the parameters of the models associated with the word "past" so that for future recognitions they are more likely to match the speech portion of "past," and would also adjust the parameters of the models associated with "has" to be less likely to match speech sounds for "past." But this is only possible if the data were correctly transcribed as the text " . . . past medical history . . . ". Instead, if the data were transcribed as the text " . . . has medical history . . . ", then the misrecognition " . . . has medical history . . . " would be deemed correct, and the parameters for the wrong models—those associated with "has"—would be adjusted to be more likely candidates for the speech sounds corresponding to "past" and the parameters for the correct models—those associated with "past"—would be adjusted so that they are not likely to be hypothesized when the speech sounds for "past" are the input. As can be seen from this example, verbatim or correct transcriptions are more essential in discriminative training than in maximum likelihood training, because incorrect transcriptions have a greater potential to negatively impact recognition accuracy in discriminative training.

Maximum mutual information estimation (MMIE) criterion-based training is one example of a technique for performing discriminative training. The methodology described here—of using the near truth transcript 1102 and thereby preventing the unreliable portions of the audio stream 302 from being used for training—may be applied just as easily to other methods of discriminative training, such as minimum classification error training (MCE) and minimum phone error training (MPE).

MMIE training maximizes the "a posteriori" probability of the word sequence corresponding to the training audio (e.g., speech sounds) given that speech. It achieves this maximization by optimizing an objective function that is a function of the likelihoods of the correct model sequence versus all model sequences for a given spoken audio stream.

Figure 13:
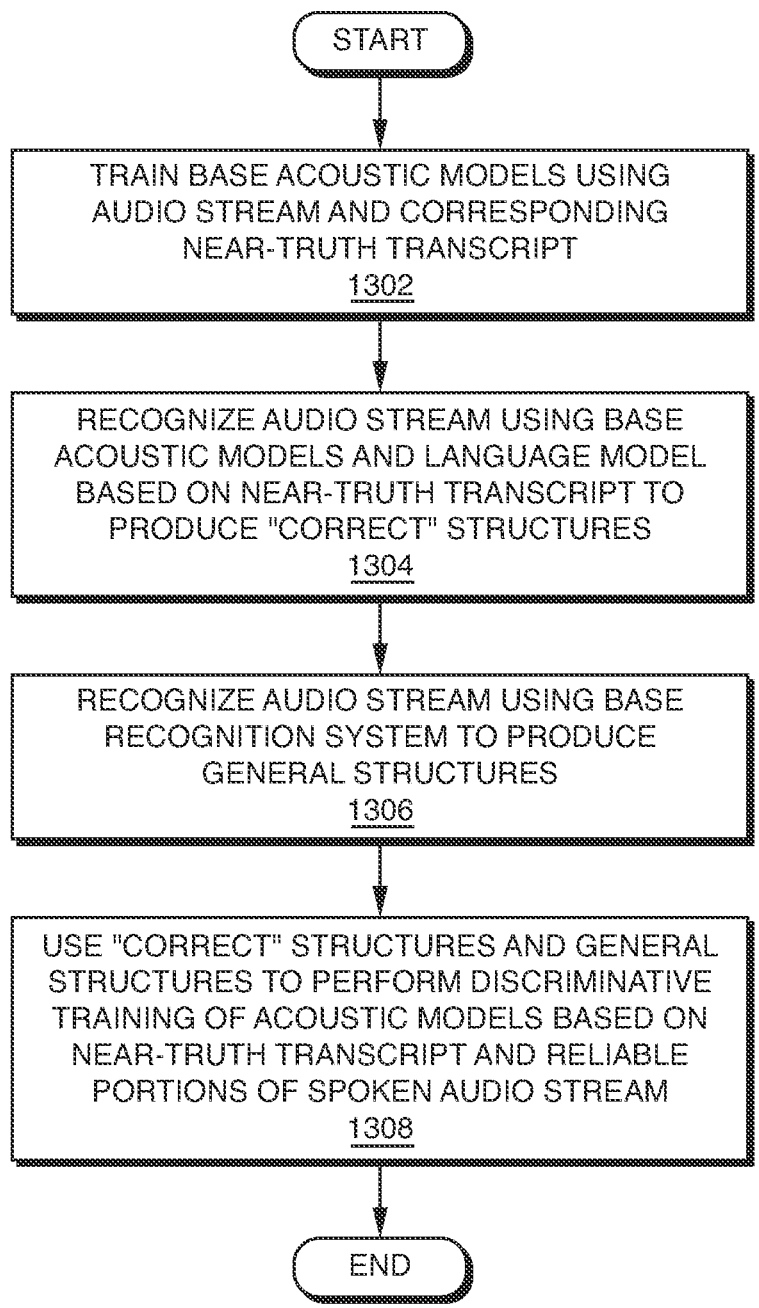
FIG. 13 is a flowchart of a method that is used in one embodiment of the present invention to train an acoustic model using discriminative training.
Figure 14:
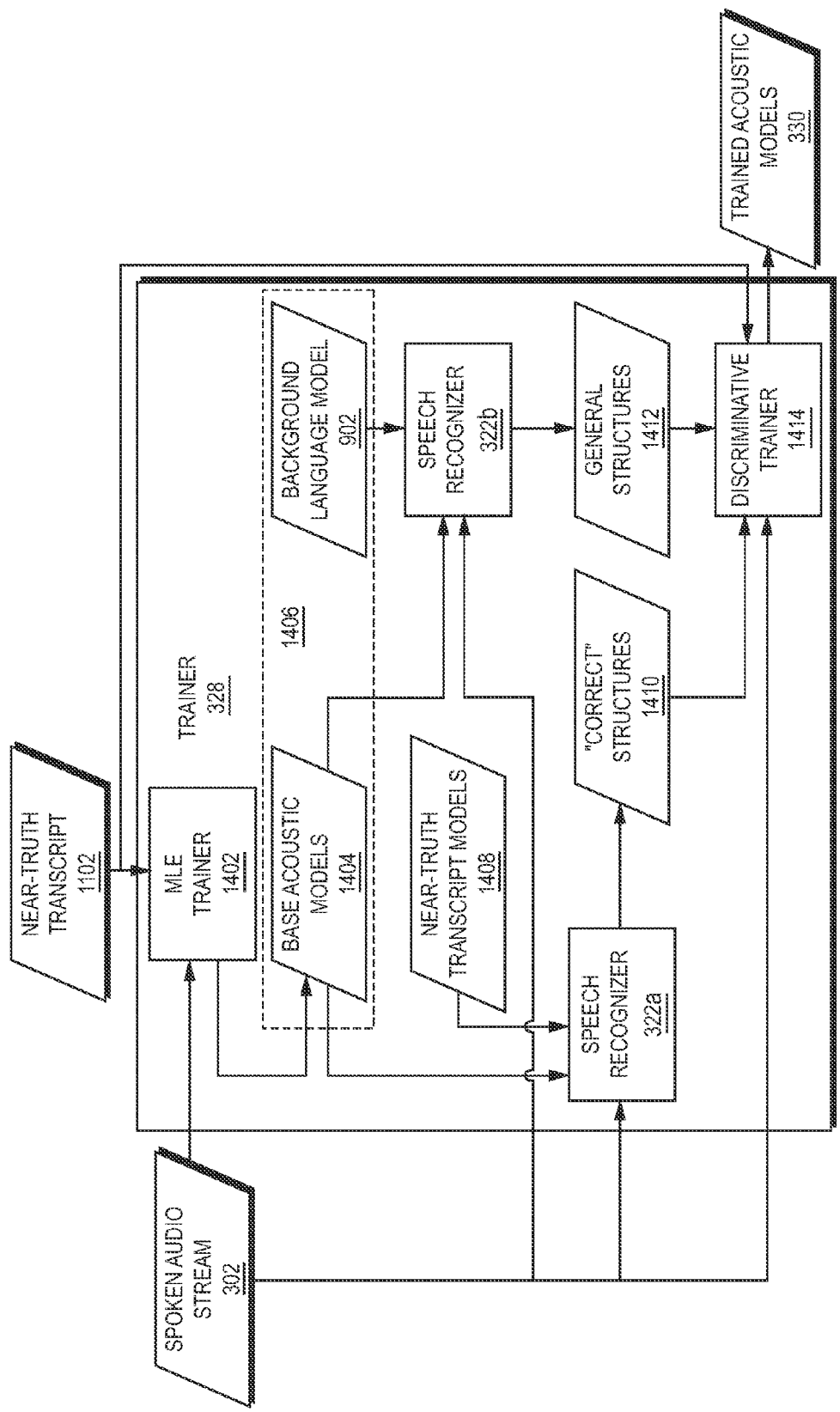
FIG. 14 is a dataflow diagram of a portion of the system of FIG. 3 which performs the method of FIG. 13 in one embodiment of the present invention.

In one embodiment, the trainer 328 trains the acoustic models 330 using discriminative training. To run any form of discriminative training, it is necessary to identify models that are trained well enough for correct recognition and models that are likely to participate in misrecognition. Such models are obtained by performing speech recognition on the training data. Referring to FIG. 13, a flowchart is shown of a method that is used in one embodiment of the present invention to train the acoustic models 330 using discriminative training. Referring to FIG. 14, a dataflow diagram is shown of a portion of the system of FIG. 3 (primarily the trainer 328) which performs the method of FIG. 13 in one embodiment of the present invention.

In the embodiment illustrated in FIGS. 13 and 14, a base recognition system 1406 is created by first using maximum likelihood estimation (MLE) training 1402 to train a base set of acoustic models 1404 using the near truth transcript 1102 (step 1302). During this training, the portions of the spoken audio stream 302 previously flagged as unreliable are ignored (not used in training). Although this step is not necessary, it is helpful to produce better quality models. Furthermore, the base set of acoustic models 1404 need not be obtained by performing MLE training. Rather, more generally the base acoustic models 1404 may be any type of model trained using any training method.

Note that the base acoustic models 1404 are not necessarily the same as the base acoustic models 324 shown in FIG. 3. Note further that although FIG. 14 shows a single audio stream 302 and a single corresponding near-truth transcript 1102, the techniques described herein with respect to FIGS. 13 and 14 may be applied to training data including a plurality of audio streams and corresponding near-truth transcripts.

The newly-trained base acoustic models 1404 and the background language model 902 are used as the basis for base recognition system 1406. Language models other than the background language model 902, if available, may be used instead. The purpose of the base recognition system 1406 is to run recognition to produce structures necessary for running discriminative training.

A speech recognizer 322a (which may be the same as speech recognizer 322) is used to align each training utterance in the spoken audio stream 302 against a recognition network of models 1408 representing the near truth transcript 1102 (step 1304). The vocabulary in this alignment is restricted to the words in the near-truth transcript 1102, and the word sequence of the transcript 1102 is reflected in the model sequence network. This process produces frame assignments which indicate mappings between frames in the spoken audio stream 302 and models in the base acoustic models.

Because unreliable portions have been filtered out of the near-truth transcript 1102, the near-truth transcript 1102 is used in this process as a proxy for a verbatim transcript. The alignment performed in step 1304 produces a first set of structures 1410 representing the "correct" recognition of the spoken audio 302. The use of quotes around the word "correct" indicates that the recognition may contain errors, but is treated as if it were correct for purposes of training. One example of the "correct" structures 1410 is the "correct" lattice used in MMIE training.

The spoken audio stream 302 is recognized using the full base recognition system 1406 (step 1306). This produces, for each utterance, the recognition structures 1412 representing the recognition output containing all possible sequences of recognized words. One example of such structures is the "general" lattice used in MMIE training.

Next, conventional discriminative training 1414 is performed on the spoken audio stream 302 using the structures 1410 and 1412 produced in the previous two recognition steps 1304 and 1306, except that the operations normally performed in discriminative training corresponding to the observation sequences or the spoken audio stream 302 are not performed for portions of the audio stream 302 previously flagged as unreliable in step 1004 (step 1308). One such operation is the computation of occupation counts with observation sequences or frames of audio. Another example is the weighting of the training data depending on the probability or likelihood for the corresponding models.

Many discriminative training techniques, such as MMI training, perform iterations in which the same structures are used in each generation. It is possible, however, to generate structures using the models trained after each iteration, and thereby to use different structures in different iterations.

Even though MMIE training has been cited as an example above, this is not a limitation of the present invention. Other forms of discriminative training, such as Minimum Phone Error training and Minimum Classification Error training, may alternatively be used. Furthermore, it is possible to use smoothing techniques to combine maximum likelihood training with discriminative training, as is well-known to those having ordinary skill in the art.

The process of filtering may also be used to discover additional spoken forms for concepts. Recall from FIG. 5 that the grammar identifier 310 may include a plurality of grammars 520a-n for a plurality of concepts. When filtering is performed, the filter 1100 may determine that although some particular concept text in the improved transcript 326 does not match the corresponding text in the normalized grammar transcript 710, the corresponding text nonetheless contains elements of the concept represented by the concept text and may therefore indicate an additional spoken form of the concept. For example, assume that the improved transcript 326 contains the text "ten one ninety three" but that the "date" grammar (e.g., grammar 520a) in the grammar repository 522 does not include a spoken form having the format "MM D YY". The filter 1100 may nonetheless recognize that the text "ten one ninety three" contains the required elements for a date, namely three numbers representing a month, a date, and a year, albeit not in the sequence specified by any of the recognized spoken forms for a date. In response, the filter 1100 may flag the text for further attention. More generally, the filter 1100 may flag text for further attention if the same text repeatedly appears in the normalized grammar transcript 710 instead of text that is expected. For example, if the expected cue for the assessment section 1226 is "Assessment," but the recognized document 326 repeatedly contains "Conclusions" as the cue for the assessment section 1226, the filter 1100 may flag such text for further attention. The filter 1100 may require that such non-matching text appear some minimum number of times in the recognized document 326 for such text to be flagged.

A human operator may take any of a variety of actions in response to such a flag. For example, the operator may determine that the flagged text represents a new spoken form for the corresponding concept, and in response create a new spoken form in the corresponding grammar based on the written form of the text. For example, the operator may add the word "conclusions" as an additional spoken form in the "assessment section cue" grammar.

Various intermediate and final results of the processes described above may be fed back into subsequent iterations of the processes to improve their future performance. For example, the base acoustic model 324 may be replaced with the trained acoustic model 330 in a subsequent iteration of the process, thereby improving the quality of the improved transcript 326 produced by the speech recognizer 322, which in turn may improve the quality of the trained acoustic model 330 produced in the subsequent iteration. Similarly, any language model that is trained by the trainer 328 may be used to replace the background language model 902, which may improve the quality of subsequent training for the same reasons. At each iteration, the speech recognizer 322 may be applied against a set of testbed audio recordings to produce recognition results and the quality of the results measured. Subsequent iterations may be performed until the recognition quality converges to within a specified range.

As described above, the filtering step may produce additional spoken forms, which may in turn improve the quality of the document-specific language model, which in turn may improve the quality of the improved transcript 326, and the overall quality of the trained acoustic model 330.

The filter 1100 may also be used to improve training results in other ways. For example, the output of the filter 1100 may be analyzed to determine whether any particular words are consistently marked as mismatches by the filter 1100. The presence of a word that is consistently marked as a mismatch by the filter 1100 may indicate that the word was recognized incorrectly by the speech recognizer 322. The dictionary entry for such a word may be updated using a corresponding portion of the spoken audio stream 302, thereby improving subsequent attempts at recognizing the same word.

One advantage of embodiments of the present invention is that they enable acoustic models and language models to be trained in the absence of verbatim transcripts of speech. The ability to perform training using non-literal transcripts expands the range of documents that may be used for training, and thereby enables training quality to be improved.

For example, training techniques disclosed herein may perform training successfully even if a non-literal transcript transcribes a concept using a written form that differs from the spoken form of the concept from which the written form was derived. This is true both for semantic concepts (such as dates, times, and diagnoses) and syntactic concepts (such as sentences, paragraphs, and sections). For example, the text "10/1/1993" may be trained against the spoken forms "october one nineteen ninety three," and "one october ninety three," and "tenth of october ninety three." This decreases the amount of training data that is discarded, thereby increasing the quality of the resulting acoustic models.

Domains, such as the medical and legal domains, in which there are large bodies of pre-existing recorded audio streams and corresponding non-literal transcripts, may find particular benefit in techniques disclosed herein. Training may be performed using such pre-existing audio streams and non-literal transcripts, thereby providing high-quality acoustic models without the cost of producing new spoken audio and/or verbatim transcripts. In particular, the existence of a large amount of pre-existing data in such domains makes it possible to train high-quality speaker-specific acoustic models, a task which typically is difficult or impossible to perform in the absence of large quantities of speaker-specific data. Once such acoustic models are generated, appropriate speaker-specific acoustic models may be selected for use in recognizing the speech of individual speakers, thereby improving speech recognition accuracy in comparison to recognition performed using speaker-independent acoustic models.

It should be mentioned that because of the generation of near-truth transcripts and the associated minimal data loss, it is possible to use discriminative techniques, which require large amounts of data in order to produce higher quality acoustic models, whether speaker-independent or speaker-specific.

Speaker-dependent language models may be generated using the large amount of pre-existing data that often exists in various domains. Referring again to FIG. 9, the background language model 902, for example, may be a speaker-dependent language model that is generated based on a large number of documents representing the speech of a particular speaker. Alternatively, the background language model 902 may be a speaker-independent language model, and an additional speaker-dependent language model may be generated. This additional speaker-dependent language model may then be interpolated with both the (speaker-independent) background language model 902 and the document-specific language model 320 to produce the interpolated language model 906. The use of speaker-dependent language models typically improves the accuracy of speech recognition when applied to speech of the same speaker.

Furthermore, techniques disclosed herein may be applied within such domains without requiring any changes in the existing process by which audio is recorded and transcribed. In the medical domain, for example, doctors may continue to dictate medical reports in their current manner, and transcripts of such reports may be produced in the current manner. Any new audio recordings and corresponding transcripts produced in this way may be used for training in the manner disclosed herein. Alternative techniques requiring changes in workflow, such as techniques which require speakers to enroll (by reading training text), require speakers to modify their manner of speaking (such as by always speaking particular concepts using predetermined spoken forms), or require transcripts to be generated in a particular format, may be prohibitively costly to implement in domains such as the medical and legal domains. Such changes might, in fact, be inconsistent with institutional or legal requirements related to report structure (such as those imposed by insurance reporting requirements). The techniques disclosed herein, in contrast, allow the audio stream 302 and corresponding non-literal transcript 304 to be generated in any manner and to have any form.

In particular, techniques disclosed herein may operate independently of and subsequent to the process by which the original audio stream 302 and corresponding non-literal transcript 304 were created. For example, the system 300 need not be used to create the non-literal transcript based 304 on the audio stream 302, or vice versa. The non-literal transcript 304 may, for example, have been generated by a human transcriptionist prior to implementation and use of the system 300 in a particular setting. Techniques disclosed herein, therefore, are independent not only of the structure and content of the audio stream 302 and transcript 304, but also of the processes by which the audio stream 302 and transcript 304 were created.

As described above, techniques disclosed herein may identify multiple alternative spoken forms of a concept. This ability is useful in several ways. For example, the ability to identify multiple spoken forms of a concept enables the document-specific language model 320 to reflect multiple spoken forms of concepts, which in turn enables the speech recognizer 322 to recognize speech in the audio stream 302 accurately even if the concepts in the audio stream 302 take different spoken forms than the same concepts in the original non-literal transcript 304. The result is that the improved transcript 326 represents a more accurate transcript of the spoken audio stream 302 than would be possible if the document-specific language model 320 did not reflect multiple spoken forms. This helps to solve the problem caused by lack of alignment between the non-literal transcript 304 and the audio stream 302, because the improved transcript 326 is likely to be more closely aligned than the non-literal transcript 304 with the audio stream 302. This improves training to the extent that training requires alignment between the training audio and the training text.

In addition to identifying alternative spoken forms, techniques disclosed herein assign probabilities to the spoken forms. The assigned probabilities may, for example, be based on the relative frequency of occurrence of the spoken forms in the non-literal transcript 304 or in other training text. Such probabilities allow the actual spoken forms in the audio stream 302 to be identified more accurately, even if the spoken forms in the audio stream 302 do not match the spoken forms in the non-literal transcript 304. Such increased recognition accuracy improves the quality of the trained acoustic models 330 for all of the reasons described above.

The use of finite state grammars to implement concepts having alternative spoken forms enables a wide range of concepts to be recognized. As described above, such concepts include both semantic concepts and syntactic concepts. There is no limitation on the number of spoken forms that may be recognized for a particular concept, or on the degree of variation among spoken forms for a particular concept. As a result, essentially any concept having any set of alternative spoken forms may be implemented using techniques disclosed herein.

Improved alignment enables less training data to be discarded by filtering than in previous systems. Furthermore, recall that prior art systems tend to systematically discard training data that do not take the same form as the transcript text. The filtering techniques disclosed herein avoid this problem by enabling speech to be used in training even if the spoken form of the speech deviates from the corresponding written form in the training text. In particular, the use of grammars representing multiple spoken forms enables speech having any of those forms to be used in training, thereby increasing the efficiency and quality of training compared to previous systems.

Furthermore, the filter 1100 performs filtering by comparing the improved transcript 326 to the normalized grammar transcript 710, rather than by filtering out results in the improved transcript 326 based on recognition confidence measures. Because the normalized grammar transcript 710 includes alternative spoken forms for concepts, such alternative spoken forms may be used by the filter 1100 to match text in the improved transcript 326 and thereby to avoid filtering out text from the improved transcript 326 simply because it appears in a different spoken form than the corresponding text in the non-literal transcript 304. This additional use of alternative spoken forms further improves the results of training. Note, however, that even if the filter 1100 were to perform filtering using the conventional approach based solely on confidence measures, the resulting near-truth transcript 1102 would still likely be more accurate than the original non-literal transcript 304 due to the use of alternative spoken forms in the speech recognition process itself.

As described above with respect to FIGS. 8-9, the speech recognizer 322 may use an interpolated language model 906 to perform speech recognition. The use of an interpolated language model 906 may improve the quality of the improved transcript 326, and thereby the quality of the acoustic model 330, in comparison to a system which used only the document-specific language model 320. More specifically, the background language model 902 provides a breadth of coverage which is not provided by the document-specific language model 320, while the document-specific language model 320 provides more detailed information about the likely content of the audio stream 302. Interpolating these two language models 902 and 320 produces a language model which has the advantageous characteristics of both.

When training is performed by the trainer (e.g., FIG. 10, step 1006), any regions in the improved transcript 326 which have been marked (e.g., by the filter 1100) as not matching the transcript 710 may be ignored, because such regions likely represent text which does not match the corresponding portion of the audio stream 302. Note, however, that through the use of the finite state grammars in the normalized grammar transcript 710, text in the improved transcript 326 which represents a different spoken form than text in the original non-literal transcript 304 need not be discarded, but rather may be used in training. This result differs from that which would be obtained if conventional training techniques were employed, because such techniques (as described above) typically discard training data resulting from attempting to train text representing one spoken form against audio in a different spoken form. The quality of training in the embodiments disclosed herein is thereby improved.

Statistics of frequent mismatches between the improved transcript 326 and the normalized grammar transcript 710 collected over a large number of training documents can be used to identify spoken language effects that are poorly covered by the current spoken form grammars 522. Those statistics can be used to automatically or manually add new (not yet covered) variations for existing concepts, or to identify the need for the entirely new concepts. The same statistics can help to identify dictionary problems (such as missing canonical forms or a new pronunciation variant that is specific to a given speaker or speaker sub-population), which are otherwise hard to find.

The techniques disclosed herein may be used advantageously in conjunction with the techniques disclosed in the above-referenced patent application entitled, "Automated Extraction of Semantic Content and Generation of a Structured Document from Speech." For example, using the techniques disclosed herein to identify the correspondence between written concepts and their spoken forms assists in the process of converting text generated by a speech recognition engine into a written form suitable for creating a structured document using the techniques disclosed in the above-referenced patent application.

It is to be understood that although the invention has been described above in terms of particular embodiments, the foregoing embodiments are provided as illustrative only, and do not limit or define the scope of the invention. Various other embodiments, including but not limited to the following, are also within the scope of the claims. For example, elements and components described herein may be further divided into additional components or joined together to form fewer components for performing the same functions.

Although the term "transcript" is used herein to characterize various documents (such as the non-literal transcript 304 and the grammar version 316 of the transcript 304), such documents need not be "transcripts" of the audio stream 302. In particular, such documents need not be produced based on the audio stream 302. Rather, in general the "transcripts" described herein may be any documents which represent information contained in the audio stream 302. Such documents may, however, contain some information which is not contained in the audio stream 302, and the audio stream 302 may contain some information which is not in such documents. Such documents may be generated before or after the audio stream 302 is generated. Although such documents may be generated based on the audio stream 302, such as through transcription, the audio stream 302 may be generated based on such documents, such as by an enrollment process.

The term "verbatim transcript of an audio stream" refers to a document that includes a word-for-word transcription of the audio stream. The term "non-literal transcript of an audio stream" refers to any document which is not a verbatim transcript of the audio stream, but which includes at least some of the same information as the audio stream.

Although the spoken audio stream 302 is described above as a "recorded" audio stream, this is not a limitation of the present invention. Rather, the audio stream 302 may be any audio stream, such as a live audio stream received directly or indirectly (such as over a telephone or IP connection), or an audio stream recorded on any medium and in any format.

In the examples above, a distinction may be made between "finite state grammars" and "text." It should be appreciated that text may be represented as a finite state grammar, in which there is a single spoken form having a probability of one. Therefore, documents which are described herein as including both text and grammars may be implemented solely using grammars if desired. Furthermore, a finite state grammar is merely one kind of context-free grammar, which is a kind of language model that allows multiple alternative spoken forms of a concept to be represented. Therefore, any description herein of techniques that are applied to finite state grammars may be applied more generally to any other kind of context-free grammar.

Although the examples above only refer to language model interpolation involving the interpolation of one background language model with one document-specific language model, the background language model may include multiple language models, such as a general medicine model, a specialty model (e.g., radiology), and a speaker-specific model. It is also possible to select a set of documents that are similar to or otherwise related to the non-literal transcript 304, and to build a document-related background language model based on this set of related documents.

In the embodiment described above with respect to FIGS. 6-7, the flat text generator 712 replaces grammars in the normalized grammar transcript 710 with flat text to produce the normalized text transcript 714. Note, however, that this step is not a requirement of the present invention. For example, the flat text generator 712 and the normalized text transcript may be omitted. In other words, grammars in the normalized grammar transcript 710 need not be replaced with flat text. Rather, the grammars may remain embedded in the normalized grammar transcript 710, and the document-specific language model 320 may be generated based on the normalized grammar transcript 710, so long as the speech recognizer 322 is capable of performing speech recognition based on embedded grammars.

The techniques described above may be implemented, for example, in hardware, software, firmware, or any combination thereof. The techniques described above may be implemented in one or more computer programs executing on a programmable computer including a processor, a storage medium readable by the processor (including, for example, volatile and non-volatile memory and/or storage elements), at least one input device, and at least one output device. Program code may be applied to input entered using the input device to perform the functions described and to generate output. The output may be provided to one or more output devices.

Each computer program within the scope of the claims below may be implemented in any programming language, such as assembly language, machine language, a high-level procedural programming language, or an object-oriented programming language. The programming language may, for example, be a compiled or interpreted programming language.

Each such computer program may be implemented in a computer program product tangibly embodied in a machine-readable storage device for execution by a computer processor. Method steps of the invention may be performed by a computer processor executing a program tangibly embodied on a computer-readable medium to perform functions of the invention by operating on input and generating output. Suitable processors include, by way of example, both general and special purpose microprocessors. Generally, the processor receives instructions and data from a read-only memory and/or a random access memory. Storage devices suitable for tangibly embodying computer program instructions include, for example, all forms of non-volatile memory, such as semiconductor memory devices, including EPROM, EEPROM, and flash memory devices; magnetic disks such as internal hard disks and removable disks; magneto-optical disks; CD-ROMs; and DVDs. Furthermore, computer program instructions may be transmitted over any of a variety of network connections using any of a variety of network protocols, and executed during and/or after transmission. Any of the foregoing may be supplemented by, or incorporated in, specially-designed ASICs (application-specific integrated circuits) or FPGAs (Field-Programmable Gate Arrays). A computer can generally also receive programs and data from a storage medium such as an internal disk (not shown) or a removable disk. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium.

What is claimed is:

1. A method for use with a system including a first document containing at least some information in common with a spoken audio stream, the method performed by at least one computer processor executing computer program instructions to perform steps of:

(A) identifying text in the first document, wherein the text represents a concept;

(B) identifying, based on the identified text and a repository of finite state grammars, a plurality of spoken forms of the concept, including at least one spoken form not contained in the first document, wherein all of the plurality of spoken forms have the same content as each other;

(C) replacing the identified text with a finite state grammar specifying the plurality of spoken forms of the concept to produce a second document;

(D) generating a document-specific language model based on the second document, comprising generating at least some of the document-specific language model based on the finite state grammar;

(E) using the document-specific language model in a speech recognition process to recognize the spoken audio stream and thereby to produce a third document;

(F) filtering text from the third document by reference to the second document to produce a filtered document in which text filtered from the third document is marked as unreliable; and (G) using the filtered document and the spoken audio stream to train an acoustic model by performing steps of:

(G)(1) applying a first speech recognition process to the spoken audio stream using a set of base acoustic models and a grammar network based on the filtered document to produce a first set of recognition structures;

(G)(2) applying a second speech recognition process to the spoken audio stream using the set of base acoustic models and a second language model to produce a second set of recognition structures; and (G)(3) performing discriminative training of the acoustic model using the first set of recognition structures, the second set of recognition structures, the filtered document, and only those portions of the spoken audio stream corresponding to text not marked as unreliable in the filtered document.

2. The method of claim 1, wherein (G) further comprises a step of:
(G)(4) prior to (G)(1), training the set of base acoustic models using the spoken audio stream and the filtered document.

3. The method of claim 2, wherein step (G)(4) comprises training the set of base acoustic models using maximum likelihood optimization training.

4. The method of claim 1, wherein the discriminative training comprises maximum mutual information estimation training, wherein the first set of recognition structures comprises a "correct" lattice, and wherein the second set of recognition structures comprises a "general" lattice.

5. A non-transitory computer-readable medium comprising computer program instructions executable by at least one computer processor to perform a method for use with a system, the system including a first document containing at least some information in common with a spoken audio stream, the method comprising:
(A) identifying text in the first document, wherein the text represents a concept;
(B) identifying, based on the identified text and a repository of finite state grammars, a plurality of spoken forms of the concept, including at least one spoken form not contained in the first document, wherein all of the plurality of spoken forms have the same content as each other;
(C) replacing the identified text with a finite state grammar specifying the plurality of spoken forms of the concept to produce a second document;
(D) generating a document-specific language model based on the second document, comprising generating at least some of the document-specific language model based on the finite state grammar;
(E) using the document-specific language model in a speech recognition process to recognize the spoken audio stream and thereby to produce a third document;
(F) filtering text from the third document by reference to the second document to produce a filtered document in which text filtered from the third document is marked as unreliable; and
(G) using the filtered document and the spoken audio stream to train an acoustic model by performing steps of: comprising:
(G)(1) applying a first speech recognition process to the spoken audio stream using a set of base acoustic models and a grammar network based on the filtered document to produce a first set of recognition structures;
(G)(2) applying a second speech recognition process to the spoken audio stream using the set of base acoustic models and a second language model to produce a second set of recognition structures; and
(G)(3) means for performing discriminative training of the acoustic model using the first set of recognition structures, the second set of recognition structures, the filtered document, and only those portions of the spoken audio stream corresponding to text not marked as unreliable in the filtered document.

6. The non-transitory computer-readable medium of claim 5, wherein (G) further comprises a step of:
(G)(4) prior to (G)(1), training the set of base acoustic models using the spoken audio stream and the filtered document.

7. The non-transitory computer-readable medium of claim 6, wherein the step (G)(4) comprises training the set of base acoustic models using maximum likelihood optimization training.

8. The non-transitory computer-readable medium of claim 5, wherein the discriminative training comprises maximum mutual information estimation training, wherein the first set of recognition structures comprises a "correct" lattice, and wherein the second set of recognition structures comprises a "general" lattice.

* * * * *

UNITED STATES PATENT AND TRADEMARK OFFICE
CERTIFICATE OF CORRECTION

PATENT NO. : 8,694,312 B2  
APPLICATION NO. : 13/773928  
DATED : April 8, 2014  
INVENTOR(S) : Lambert Mathias et al.

It is certified that error appears in the above-identified patent and that said Letters Patent is hereby corrected as shown below:

In the Drawings

On sheet 13 of 15, in Figure 12, line 4, delete "itchey" and insert -- itchy --, therefor.

In the Specification

In column 2, line 58, delete "ih ax" and insert -- ih s ax --, therefor.

In the Claims

In column 28, line 9-10, in claim 5, delete "of: comprising:" and insert -- of: --, therefor.

In column 28, line 18, in claim 5, delete "means for performing" and insert -- performing --, therefor.

Signed and Sealed this  
Ninth Day of December, 2014

Michelle K. Lee  
*Deputy Director of the United States Patent and Trademark Office*